US011098043B2

(12) United States Patent
Zhang et al.

(10) Patent No.: US 11,098,043 B2
(45) Date of Patent: Aug. 24, 2021

(54) CERTAIN IMIDAZOPYRIDINES AS CYCLIC AMP RESPONSE ELEMENT BINDING (CREB) BINDING PROTEIN (CBP) INHIBITORS AND USES THEREOF

(71) Applicant: University of Massachusetts, Boston, MA (US)

(72) Inventors: Wei Zhang, Boston, MA (US); Alex Mugwiria Muthengi, Malden, MA (US); Hailemichael O. Yosief, Cincinnati, OH (US)

(73) Assignee: University of Massachusetts, Boston, MA (US)

( * ) Notice: Subject to any disclaimer, the term of this patent is extended or adjusted under 35 U.S.C. 154(b) by 57 days.

(21) Appl. No.: 16/629,408

(22) PCT Filed: Jul. 13, 2018

(86) PCT No.: PCT/US2018/041933
§ 371 (c)(1),
(2) Date: Jan. 8, 2020

(87) PCT Pub. No.: WO2019/014514
PCT Pub. Date: Jan. 17, 2019

(65) Prior Publication Data
US 2020/0140433 A1 May 7, 2020

Related U.S. Application Data

(60) Provisional application No. 62/532,701, filed on Jul. 14, 2017.

(51) Int. Cl.
*C07D 471/04* (2006.01)
*A61P 35/00* (2006.01)
*A61P 25/28* (2006.01)

(52) U.S. Cl.
CPC ............ *C07D 471/04* (2013.01); *A61P 25/28* (2018.01); *A61P 35/00* (2018.01)

(58) Field of Classification Search
CPC ......... C07D 471/04; A16P 25/28; A61P 35/00
See application file for complete search history.

(56) References Cited

U.S. PATENT DOCUMENTS

| 6,703,404 B2 * | 3/2004 | Maul ................... | C07D 487/04 514/300 |
| 8,501,767 B2 * | 8/2013 | Bode ................... | C07D 487/04 514/300 |
| 2009/0170855 A1 | 7/2009 | Kesteleyn et al. | |
| 2010/0173930 A1 * | 7/2010 | Muci ................... | A61P 21/00 514/300 |
| 2010/0292232 A1 | 11/2010 | Elleder et al. | |
| 2011/0312957 A1 | 12/2011 | Bode et al. | |

FOREIGN PATENT DOCUMENTS

WO WO 2011/143669 11/2011

OTHER PUBLICATIONS

Ansari et al ChemistrySelect2016, 5, 1016-1021. (Year: 2016).*
International Search Report and the Written Opinion of the International Searching Authority, for PCT Appl. No. PCT/US18/41933, dated Oct. 29, 2018, 15 pages.
Bienayme et al., "A new heterocyclic multicomponent reaction for the combinatorial synthesis of fused 3-aminoimidazoles," Angewandte Chemie International Edition, Sep. 4, 1998, 37(16):2234-7.
Blackburn et al., "Parallel synthesis of 3-aminoimidazo [1, 2-a] pyridines and pyrazines by a new three-component condensation," Tetrahedron Letters, May 28, 1998, 39(22):3635-8.
Chekler et al., "Transcriptional profiling of a selective CREB binding protein bromodomain inhibitor highlights therapeutic opportunities," Chemistry & Biology, Dec. 17, 2015, 22(12):1588-96.
Crawford et al., "Discovery of a potent and selective in vivo probe (GNE-272) for the bromodomains of CBP/EP300," Journal of Medicinal Chemistry, Dec. 8, 2016, 59(23):10549-63.
Denny et al., "Structure-based design of highly selective inhibitors of the CREB binding protein bromodomain" Journal of Medicinal Chemistry, Jul. 13, 2017 60(13):5349-63.
Filippakopoulos et al., "Targeting bromodomains: epigenetic readers of lysine acetylation," Nature Reviews Drug Discovery, May 2014, 13(5):337-56.
Groebke et al., "Synthesis of imidazo [1, 2-a] annulated pyridines, pyrazines and pyrimidines by a novel three-component condensation," Synlett, Jun. 1998, vol. 1998(06):661, 1 page.
Hay et al., "Discovery and optimization of small-molecule ligands for the CBP/p300 bromodomains," Journal of the American Chemical Society, Jul. 2, 2014, 136(26):9308-19.
Hewings et al., "Progress in the development and application of small molecule inhibitors of bromodomain-acetyl-lysine interactions," Journal of Medicinal Chemistry, Nov. 26, 2012, 55(22):9393-413.
Mujtaba et al., "Structural mechanism of the bromodomain of the coactivator CBP in p53 transcriptional activation," Molecular Cell, Jan. 30, 2004, 13(2):251-63.
PCT International Preliminary Report on Patentability in International Appln. No. PCT/US2018/41933, dated Jan. 14, 2020, 8 pages.
Plotnikov et al., "Structural insights into acetylated-histone H4 recognition by the bromodomain-PHD finger module of human transcriptional coactivator CBP," Structure, Feb. 4, 2014, 22(2):353-60.
Popp et al., "Development of selective CBP/P300 benzoxazepine bromodomain inhibitors," Journal of Medicinal Chemistry, Oct. 13, 2016, 59(19):8889-912.
Rooney et al., "Series of Potent CREBBP Bromodomain Ligands Reveals an Induced-Fit Pocket Stabilized by a Cation-π Interaction," Angewandte Chemie International Edition, Jun. 2014, 53(24):6126-30.
Smith et al "The bromodomain: a new target in emerging epigenetic medicine," ACS Chemical Biology, Mar. 18, 2016, 11(3):598-608.
Taylor et al., "Fragment-based discovery of a selective and cell-active benzodiazepinone CBP/EP300 bromodomain inhibitor (CPI-637)," ACS Medicinal Chemistry Letters, May 12, 2016, 7(5):531-6.

(Continued)

*Primary Examiner* — John Mabry
(74) *Attorney, Agent, or Firm* — Fish & Richardson P.C.

(57) ABSTRACT

This disclosure relates to compounds that are CBP inhibitor and methods of using such compounds in the treatment and diagnosis of diseases and disorders.

26 Claims, 1 Drawing Sheet

(56) References Cited

OTHER PUBLICATIONS

Theodoulou et al., "Clinical progress and pharmacology of small molecule bromodomain inhibitors," Current Opinion in Chemical Biology, Aug. 1, 2016, 33:58-66.

\* cited by examiner

A
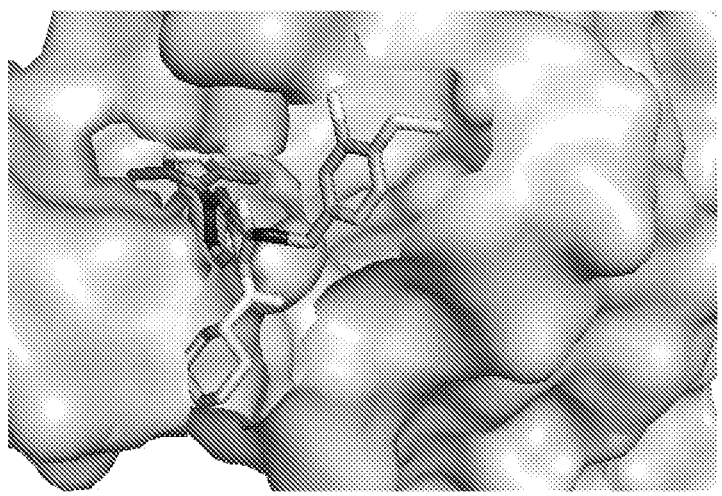
B
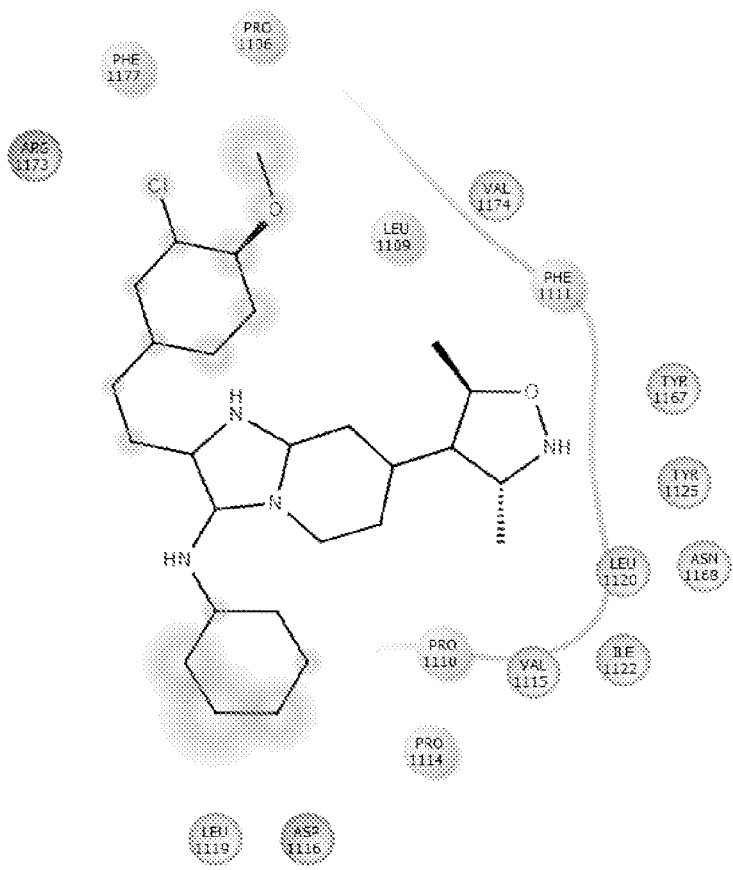

CERTAIN IMIDAZOPYRIDINES AS CYCLIC AMP RESPONSE ELEMENT BINDING (CREB) BINDING PROTEIN (CBP) INHIBITORS AND USES THEREOF

This application is a U.S. National Stage Application under 35 USC § 371 of International Patent Application Serial No. PCT/US2018/041933, filed on Jul. 13, 2018, entitled "HETEROCYCLIC COMPOUNDS AND USES THEREOF," which claims the benefit of U.S. Provisional Patent Application Ser. No. 62/532,701, filed on Jul. 14, 2017. The entire contents of the foregoing are hereby incorporated by reference.

STATEMENT REGARDING FEDERALLY SPONSORED RESEARCH OR DEVELOPMENT

This invention was made with Government support under Grant Nos. U54CA156734 awarded by the National Institutes of Health. The Government has certain rights in the invention.

FIELD

This disclosure relates to compounds that bind cyclic AMP response element binding (CREB) binding proteins and methods of using such compounds in the treatment and diagnosis of diseases and disorders.

BACKGROUND

Altered regulation of signaling pathways, gene expression, and proteome constituents are all hallmarks of cancer. These alterations, individually or in combination, can confer competitive advantages to cancer cells, e.g. evade the host immune system, gain axis to blood supply, tolerate higher levels of DNA damage, and/or suppress innate apoptotic signaling. One family of proteins that is often improperly regulated or mutated in cancer cells is the cyclic AMP response element binding (CREB) binding protein (CBP) (P. Filippakopoulos and S Knapp, Nat. Rev. Drug Disc. 13, 337-356 (2014); S. G. Smith an M-M Zhou, ACS Chem. Biol. 11, 598-608 (2016)).

SUMMARY

This disclosure provides compounds of Formula I:

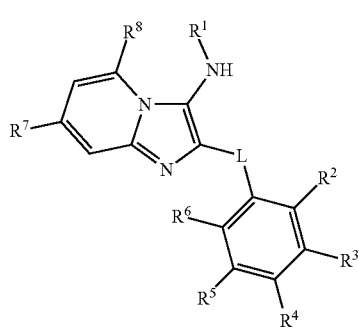

(I)

or a pharmaceutically acceptable salt thereof, wherein the constituent variables are as described herein.

This disclosure also provides pharmaceutical composition comprising a compound described herein, or a pharmaceutically acceptable salt thereof, and at least one pharmaceutically acceptable excipient.

Provided herein are also methods of inhibiting CBP activity, wherein the method comprises contacting a compound described herein, or a pharmaceutically acceptable salt thereof with CBP.

Provided herein are also methods of treating a disease or disorder associated with inhibition of CBP activity, wherein the method comprise administering to a subject in need thereof a therapeutically effective amount of a compound described herein, or a pharmaceutically acceptable salt thereof.

This disclosure also provides for treating cancer in a subject, wherein the method comprise administering to the subject a therapeutically effective amount of the compound described herein, or a pharmaceutically acceptable salt thereof.

Provided herein are also methods for treating neurodegenerative disease in a subject, wherein the method comprise administering to the subject a therapeutically effective amount of the compound described herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A and FIG. 1B show a docked complex of Compound 21 with CBP bromodomain (PDB ID: 4NR7).

DETAILED DESCRIPTION

Cyclic AMP response element binding (CREB) binding proteins (CBPs) co-activate select transcription factors by acetylating select lysine residues in target proteins and by acting as a scaffolds to stabilize molecular complexes (N. H. Theodoulou et al., Curr. Opin. Chem. Biol. 33, 58-66 (2016); D. S. Hewings et al, J. Med. Chem. 55, 9393-9413 (2012); R. A. Denny et al., J. Med. Chem. 60, 5349-5363 (2017); D. A. Hay et al., J. Am. Chem. Soc. 136, 9308-9319 (2014)). Of the transcription factors activated by CBPs, some have prominent biological roles—e.g. in cellular homeostasis (e.g. CREB), homologous recombination double-stranded DNA repair (e.g. BRCA1), cell cycle progression (e.g. c-Jun), and activation of pro-apoptotic genes (e.g. p53) (A. N. Plotnikov et al., Structure 22, 353-360 (2014); S. Mujtaba et al., Mol. Cell 13, 251-263 (2004)). Given that several critical cellular processes require CBP activity, there has been significant interest in the development of compounds that selectively bind and inhibit CBP activity with minimal off-target effects (e.g. compounds binding to proteins with similar structural motifs other than CBP) and development of methods that use CBP inhibitor compounds or compositions to treat or diagnosis cancers.

To date, synthesis and biological activity of several CBP inhibitors has been reported. The Structural Genomics Consortium (SGC) group developed two potent CBP inhibitors, CBP-30 and I-CBP112, with low nanomolar potencies for the CBP/P300 bromodomains (D. A. Hay et al., J. Am. Chem. Soc. 136, 9308-9319, 2014). CBP-30 is a CREBBP/EP300-selective chemical probe. I-CBP112 is a CREBBP/EP300-selective chemical probe. CBP-30 and I-CBP112 contain two different chemical scaffolds, the oxoazepine (ICBP112) and the slightly more potent benzimidazole (CBP30) containing 3,5-dimethylisoxazole as acetyl lysine mimic (G. Giotopoulos et al., Oncog. 35, 279-289 (2016)). Other CBP inhibitors developed by other research groups include: (R)-2 (T. P. C. Rooney et al., Angew. Chem. Int. Ed. 53, 6126-6130, 2014), PF-CBP1 (R. A. Denny et al., J. Med. Chem. 60, 5349-5363 2017; E. L. P. Chekler et ak., Chem. & Biol. 22, 1588-1596, 2015), TPO146 (T. A. Popp et al. J. Am. Chem. Soc. 59, 8889-8912, 2016), CP1-637 (A. M. Taylor et al. ACS Med. Chem. Lett. 7, 531-536, 2016) and GNE-272 (T. D. Crawford et al. J. Am. Chem. Soc. 59, 10549-10563, 2016). While the aforementioned compounds bind CBP with $K_d$ values in the nanomolar range, the compounds also bind proteins other than CBP such as BRD4, a representative off-target binding partner for the CBP inhibitors. Thus, the aforementioned compounds are not sufficiently selective for CBP and may cause unwanted, off-target effects when used as drugs to treat mammalian cells in vivo or in cell culture.

Provided in this disclosure are compounds with high selectivity for CBP are detailed, and process and methods of use of the same. The activity and selectivity of the compounds provided are assessed by measuring binding strengths of the compounds for CBP and for an off-target protein (e.g. BRD4) using in vitro binding assays. The compounds provided herein are selective CBP inhibitor and can be a potent agent against cells with upregulated CBP activity, e.g., cancers and neurodegenerative diseases. Compounds provided herein can be prepared in two steps (e.g., Groebke-Blackburn-Bienayme multicomponent reaction followed by Suzuki coupling), which has high atom- and step economy. The CBP selective compounds provided herein are useful for the treatment of cancers and neurodegenerative diseases.

Provided herein are compounds of Formula I:

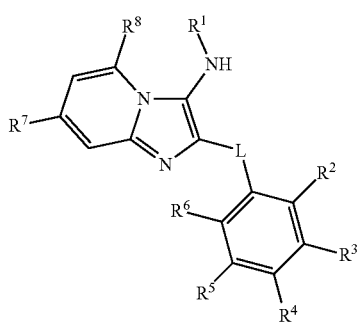

(I)

or a pharmaceutically acceptable salt thereof, wherein:

L is $(CR^aR^b)_n$;

$R^a$ and $R^b$ are each independently selected from H, $C_{1-8}$ alkyl, $C_{2-8}$ alkenyl, and $C_{2-8}$ alkynyl;

n is 0, 1, 2, or 3;

$R^1$ is selected from $C_{1-8}$ alkyl, $C_{2-8}$ alkenyl, $C_{2-8}$ alkynyl, $C_{1-6}$ haloalkyl, C(O)H, C(O)($C_{1-8}$ alkyl), C(O)OH, C(O)O ($C_{1-8}$ alkyl), $C_{3-10}$ cycloalkyl, $C_{3-10}$ cycloalkyl-$C_{1-4}$ alkylene, 4-10 membered heterocycloalkyl, 4-10 membered heterocycloalkyl-$C_{1-4}$ alkylene, $C_{6-10}$ aryl, $C_{6-10}$ aryl-$C_{1-4}$ alkylene, 5-10 membered heteroaryl, and 5-10 membered heteroaryl-$C_{1-4}$ alkylene; wherein the 4-10 membered heterocycloalkyl, 4-10 membered heterocycloalkyl-$C_{1-4}$ alkylene, 5-10 membered heteroaryl, and 5-10 membered heteroaryl-$C_{1-4}$ alkylene each has at least one ring-forming carbon atom and 1, 2, 3, or 4 ring-forming heteroatoms independently selected from N, O, and S; wherein the N and S are optionally oxidized; and wherein the $C_{1-8}$ alkyl, $C_{2-8}$ alkenyl, $C_{2-8}$ alkynyl, $C_{3-10}$ cycloalkyl, $C_{3-10}$ cycloalkyl-$C_{1-4}$ alkylene, 4-10 membered heterocycloalkyl, 4-10 membered heterocycloalkyl-$C_1$-4 alkylene, $C_{6-10}$ aryl, $C_{6-10}$ aryl-$C_{1-4}$ alkylene, 5-10 membered heteroaryl, and 5-10 membered heteroaryl-$C_{1-4}$ alkylene are each optionally substituted with 1, 2, or 3 substituents selected from halo, C(O)H, C(O)($C_{1-8}$ alkyl), C(O)OH, and C(O)O($C_{1-8}$ alkyl);

$R^2$, $R^3$, $R^4$, $R^5$, and $R^6$ are each independently selected from H, halo, $C_{1-s}$ alkyl, $C_{2-8}$ alkenyl, $C_{2-8}$ alkynyl, $C_{1-8}$ haloalkyl, OH, and O—$C_{1-8}$ alkyl;

$R^7$ is selected from Cy, $C_{1-8}$ alkyl, $C_{2-8}$ alkenyl, and $C_{2-8}$ alkynyl;

$R^8$ is selected from H, $C_{1-8}$ alkyl, $C_{2-8}$ alkenyl, and $C_{2-8}$ alkynyl; and Cy is selected from 4-10 membered heterocycloalkyl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; and wherein the 4-10 membered heterocycloalkyl and 5-10 membered heteroaryl are each optionally substituted with 1, 2, 3 or 4 substituents independently selected from oxo, $C_{1-8}$ alkyl, $C_{2-8}$ alkenyl, and $C_2$-alkynyl.

In some embodiments, the compound is of Formula II:

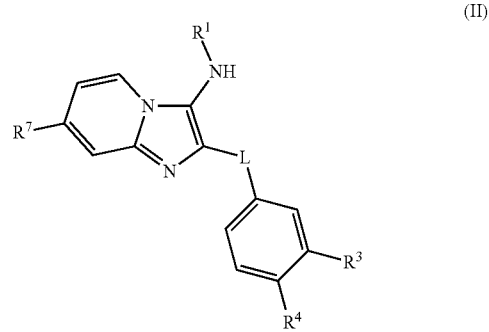

(II)

or a pharmaceutically acceptable salt thereof.

In some embodiments, the compound is of Formula III:

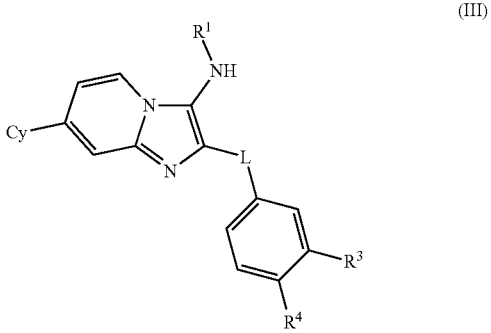

(III)

or a pharmaceutically acceptable salt thereof.

In some embodiments, the compound is of Formula IV:

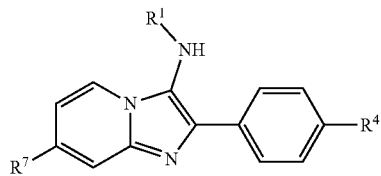
(IV)

or a pharmaceutically acceptable salt thereof.

In some embodiments, the compound is of Formula V:

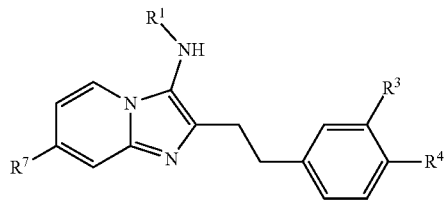
(V)

or a pharmaceutically acceptable salt thereof.

In some embodiments, n is 0. In some embodiments, n is 1. In some embodiments, n is 2. In some embodiments, n is 3.

In some embodiments, $R^a$ is H. In some embodiments, $R^a$ is $C_{1-8}$ alkyl (e.g., methyl, ethyl, n-propyl, isopropyl, n-butyl, t-butyl, etc.).

In some embodiments, $R^b$ is H. In some embodiments, $R^b$ is $C_{1-8}$ alkyl (e.g., methyl, ethyl, n-propyl, isopropyl, n-butyl, t-butyl, etc.).

In some embodiments, $R^1$ is selected from $C_{1-8}$ alkyl, $C_{3-10}$ cycloalkyl, $C_{3-10}$ cycloalkyl-$C_{1-4}$ alkylene, 4-10 membered heterocycloalkyl, 4-10 membered heterocycloalkyl-$C_{1-4}$ alkylene, $C_{6-10}$ aryl, $C_{6-10}$ aryl-$C_{1-4}$ alkylene, 5-10 membered heteroaryl, and 5-10 membered heteroaryl-$C_{1-4}$ alkylene; wherein the 4-10 membered heterocycloalkyl, 4-10 membered heterocycloalkyl-$C_{1-4}$ alkylene, 5-10 membered heteroaryl, and 5-10 membered heteroaryl-$C_{1-4}$ alkylene each has at least one ring-forming carbon atom and 1, 2, 3, or 4 ring-forming heteroatoms independently selected from N, O, and S; wherein the N and S are optionally oxidized; and wherein the $C_{1-8}$ alkyl, $C_{2-8}$ alkenyl, $C_{2-8}$ alkynyl, $C_{3-10}$ cycloalkyl, $C_{3-10}$ cycloalkyl-$C_{1-4}$ alkylene, 4-10 membered heterocycloalkyl, 4-10 membered heterocycloalkyl-$C_{1-4}$ alkylene, $C_{6-10}$ aryl, $C_{6-10}$ aryl-$C_{1-4}$ alkylene, 5-10 membered heteroaryl, and 5-10 membered heteroaryl-$C_{1-4}$ alkylene are each optionally substituted with 1, 2, or 3 substituents selected from halo, C(O)H, C(O)($C_{1-8}$ alkyl), C(O)OH, and C(O)O($C_{1-8}$ alkyl).

In some embodiments, $R^1$ is $C_{1-8}$ alkyl optionally substituted with 1, 2, or 3 substituents selected from halo, C(O)H, C(O)($C_{1-8}$ alkyl), C(O)OH, and C(O)O($C_{1-8}$ alkyl).

In some embodiments, $R^1$ is $C_{1-8}$ alkyl optionally substituted with 1 C(O)O($C_{1-8}$ alkyl). In some embodiments, $R^1$ is selected from:

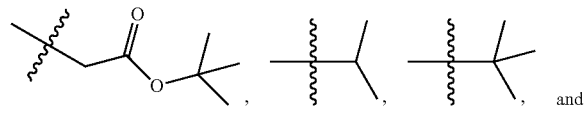
,

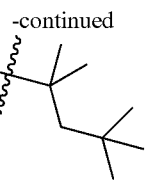
, wherein the wavy line denotes the point of attachment to the amino nitrogen. In some embodiments, $R^1$ is

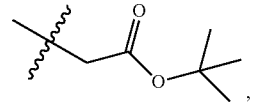 [SMILES: *CC(=O)OC(C)(C)C ; ","]
, wherein the wavy line denotes the point of attachment to the amino nitrogen.

In some embodiments, $R^1$ $C_{3-10}$ cycloalkyl. In some embodiments, $R^1$ is

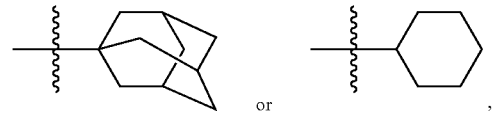 [SMILES: *C12CC3CC(CC(C3)C1)C2 ; "or" ; *C1CCCCC1 ; ","]

wherein the wavy line denotes the point of attachment to the amino nitrogen. In some embodiments, $R^1$ is

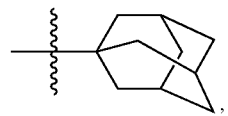
, wherein the wavy line denotes the point of attachment to the amino nitrogen.

In some embodiments, $R^1$ is 4-10 membered heterocycloalkyl or 4-10 membered heterocycloalkyl-$C_{1-4}$ alkylene. In some embodiments, $R^1$ is 4-10 membered heterocycloalkyl-$C_{1-4}$ alkylene. In some embodiments, $R^1$ is

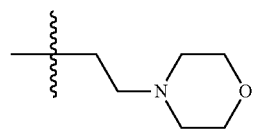 [SMILES: *CCN1CCOCC1]

wherein the wavy line denotes the point of attachment to the amino nitrogen.

In some embodiments, $R^1$ is $C_{6-10}$ aryl or $C_{6-10}$ aryl-$C_{1-4}$ alkylene. In some embodiments, $R^1$ is phenyl.

In some embodiments, $R^2$, $R^3$, $R^4$, $R^5$, and $R^6$ are each independently selected from H, halo, $C_{1-8}$ alkyl, OH, and O—$C_{1-8}$ alkyl. In some embodiments, $R^2$, $R^3$, $R^4$, $R^5$, and $R^6$ are H. In some embodiments, $R^2$, $R^5$, and $R^6$ are each H.

In some embodiments, $R^3$ is halo, $C_{1-8}$ alkyl, OH, and O—$C_{1-8}$ alkyl. In some embodiments, $R^3$ is halo. In some embodiments, $R^3$ is fluoro or chloro. In some embodiments, $R^3$ is fluoro. In some embodiments, $R^3$ is chloro. In some embodiments, $R^3$ is $C_{1-8}$ alkyl. In some embodiments, $R^3$ is methyl, ethyl, n-propyl, isopropyl, n-butyl, or t-butyl. In some embodiments, $R^3$ is O—$C_{1-8}$ alkyl. In some embodiments, $R^3$ is methoxy. In some embodiments, $R^3$ is ethoxy.

In some embodiments, $R^4$ is halo, $C_{1-8}$ alkyl, OH, and O—$C_{1-8}$ alkyl. In some embodiments, $R^4$ is halo. In some embodiments, $R^4$ is fluoro or chloro. In some embodiments, $R^4$ is fluoro. In some embodiments, $R^4$ is chloro. In some embodiments, $R^4$ is $C_{1-8}$ alkyl. In some embodiments, $R^4$ is methyl, ethyl, n-propyl, isopropyl, n-butyl, or t-butyl. In some embodiments, $R^4$ is O—$C_{1-8}$ alkyl. In some embodiments, $R^4$ is methoxy. In some embodiments, $R^4$ is ethoxy.

In some embodiments, $R^7$ is $C_{1-8}$ alkyl. In some embodiments, wherein $R^7$ is methyl.

In some embodiments, $R^7$ is Cy. In some embodiments, Cy is selected from 4-10 membered heterocycloalkyl optionally substituted with 1, 2, 3 or 4 substituents independently selected from oxo, $C_{1-8}$ alkyl, $C_{2-8}$ alkenyl, and $C_{2-8}$ alkynyl. In some embodiments, Cy is 5-10 membered heteroaryl optionally substituted with 1, 2, 3 or 4 substituents independently selected from oxo, $C_{1-8}$ alkyl, $C_{2-8}$ alkenyl, and $C_{2-8}$ alkynyl.

In some embodiments, Cy is isoxazolyl, indazolyl, 3,4-dihydroquinazolin-2(1H)-onyl, or 3a,7a-dihydrobenzo[d]isoxazolyl. In some embodiments, Cy is isoxazolyl. In some embodiments, Cy is indazolyl. In some embodiments, Cy is 3,4-dihydroquinazolin-2(1H)-onyl. In some embodiments, Cy is 3a,7a-dihydrobenzo[d]isoxazolyl.

In some embodiments, Cy is

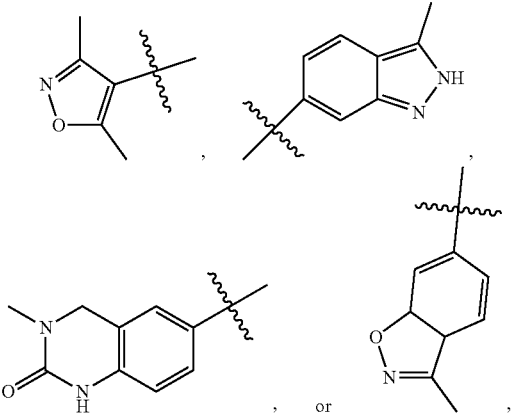

wherein the wavy line denotes the point of attachment to the imidazo[1,2-a]pyridine.

In some embodiments, Cy is

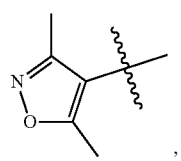 [SMILES: *c1c(C)noc1C ; ","]

wherein the wavy line denotes the point of attachment to the imidazo[1,2-a]pyridine.

In some embodiments, Cy is

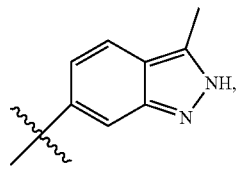 [SMILES: *c1ccc2c(C)[nH]nc2c1]

wherein the wavy line denotes the point of attachment to the imidazo[1,2-a]pyridine.

In some embodiments, Cy is

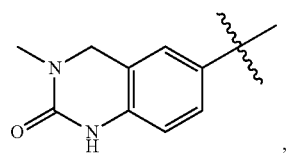 [SMILES: *c1ccc2c(c1)CN(C)C(=O)N2 ; ","]

wherein the wavy line denotes the point of attachment to the imidazo[1,2-a]pyridine.

In some embodiments, Cy is

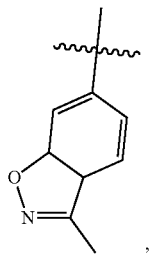 [SMILES: *C1=CC2ON=C(C)C2C=C1 ; ","]

wherein the wavy line denotes the point of attachment to the imidazo[1,2-a]pyridine.

In some embodiments, $R^8$ is H or $C_{1-8}$ alkyl.

In some embodiments, $R^8$ is H.

In some embodiments, the compound is selected from:

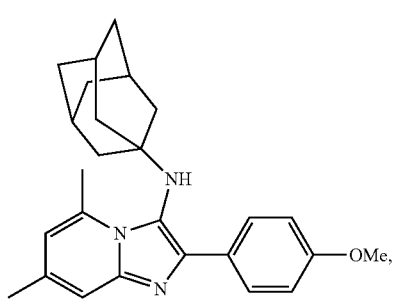

-continued
2
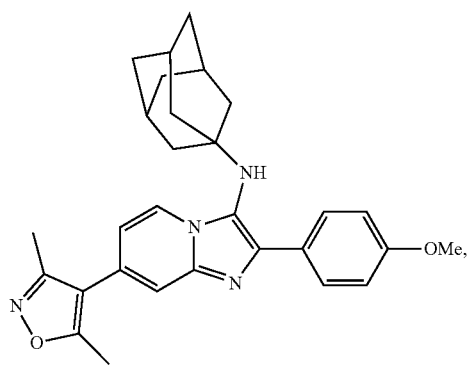
3
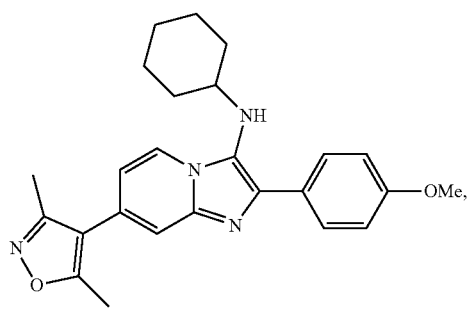
4
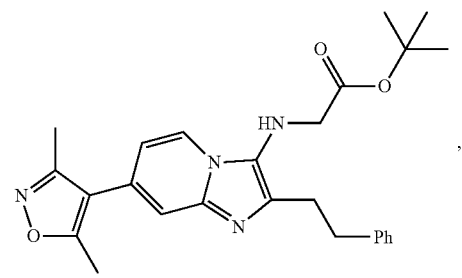
5
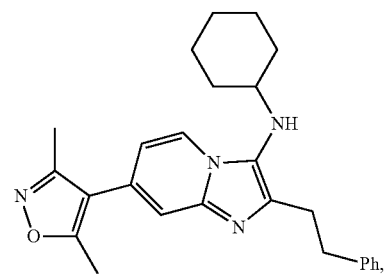
6
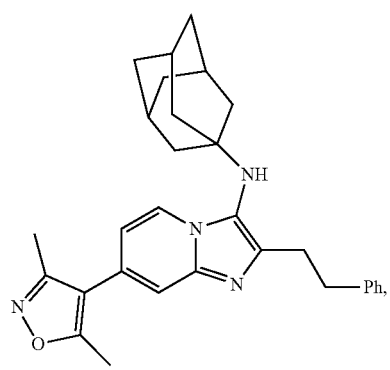
-continued
7
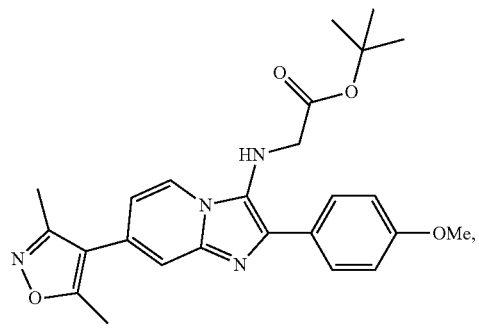
8
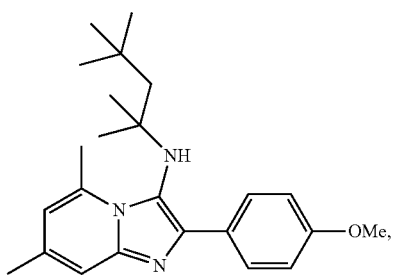
9
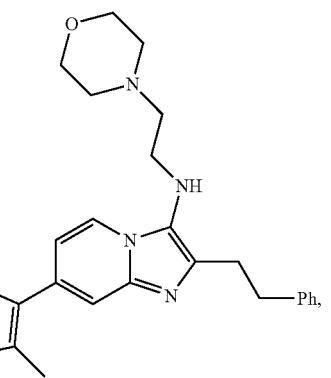
10
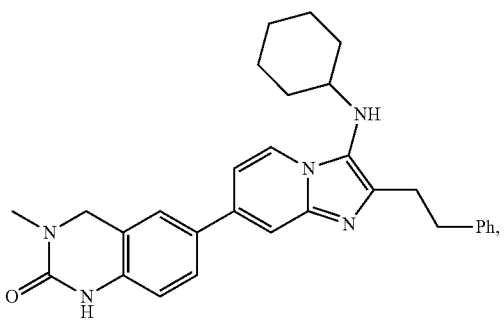
11
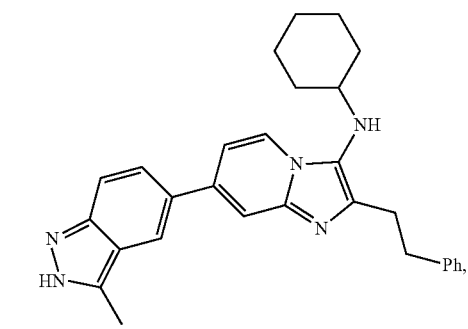

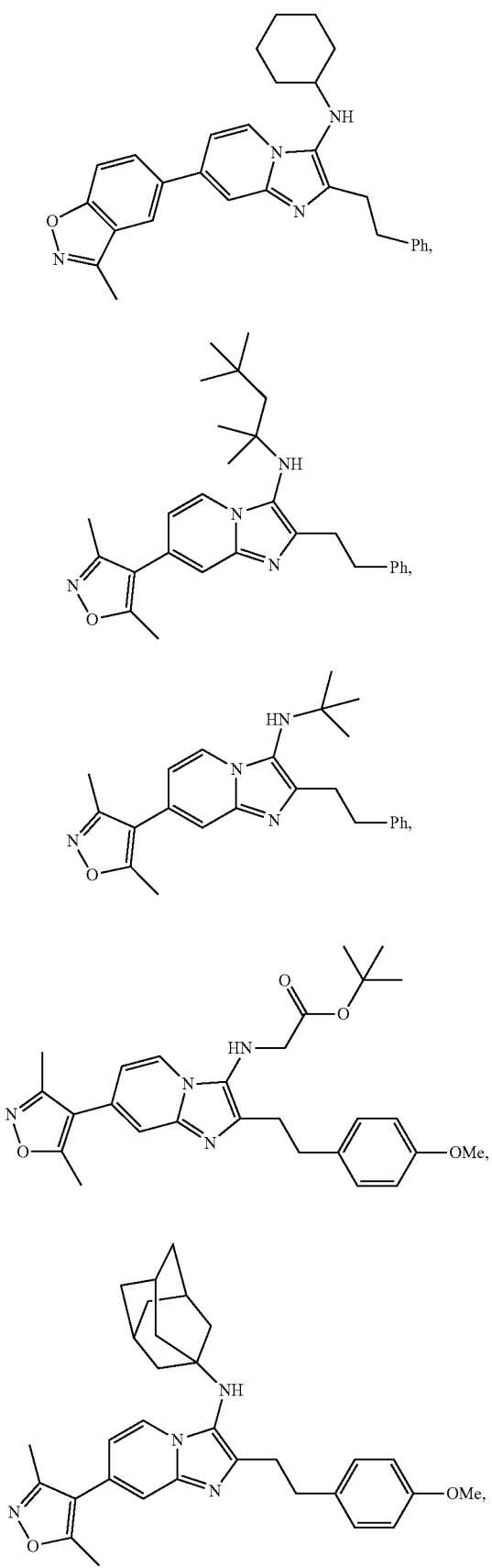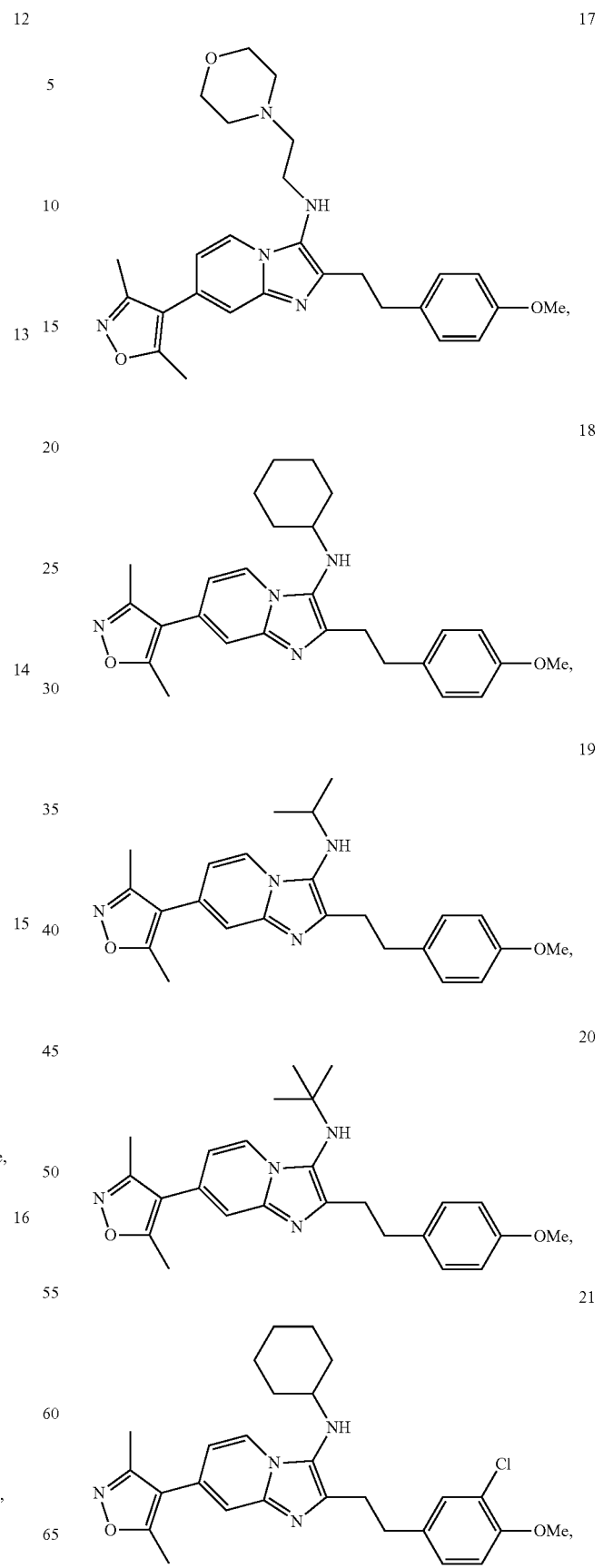

22
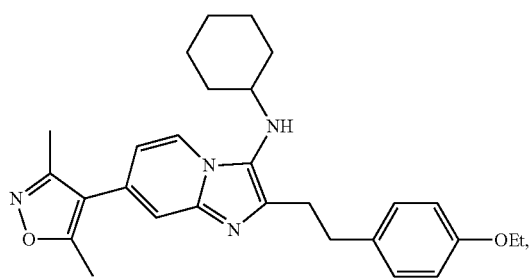
23
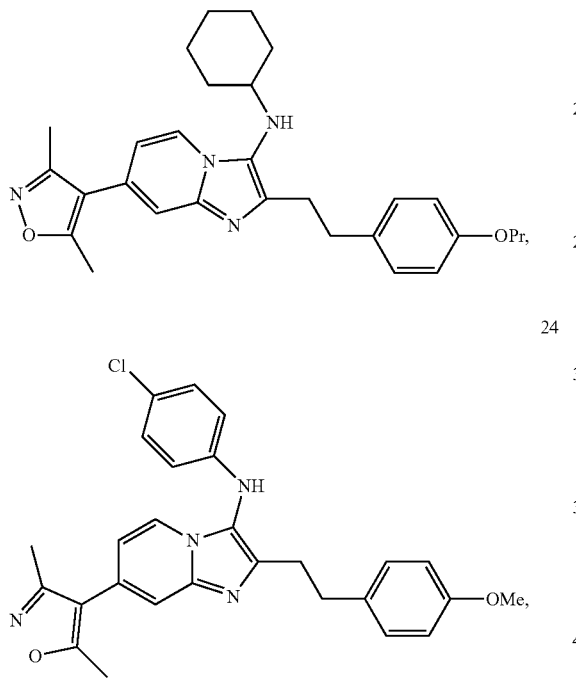
24
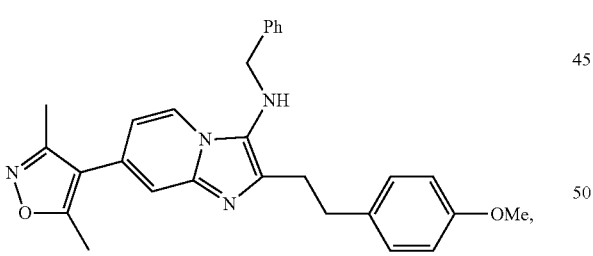
24
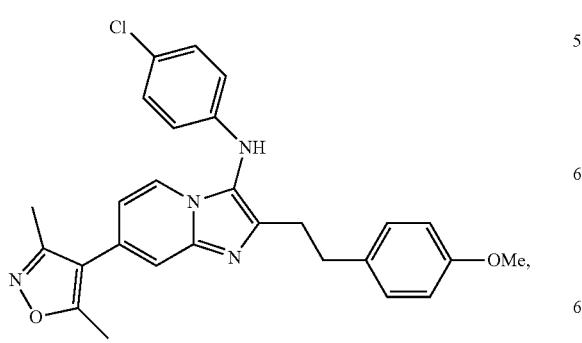
25
26
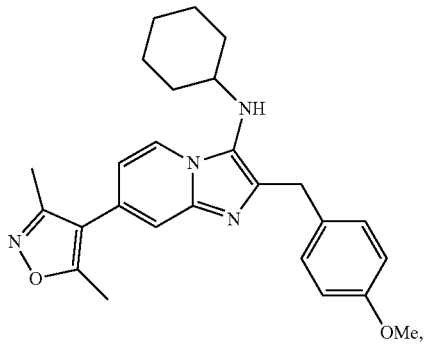
27
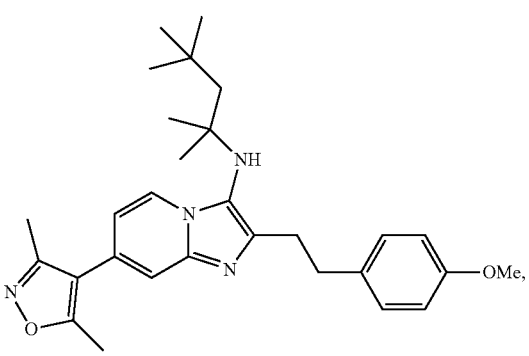
28
29
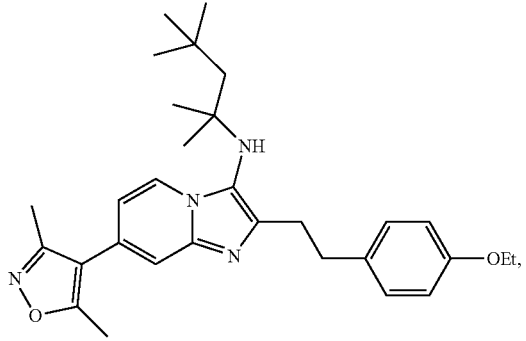

or a pharmaceutically acceptable salt thereof.

In some embodiments, the compound is

-continued

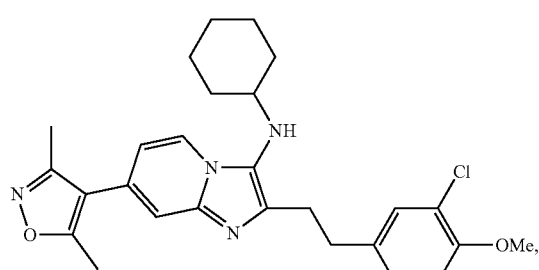

21 or a pharmaceutically acceptable salt thereof.

Compounds described herein can be synthesized according to Scheme 1.

Scheme I

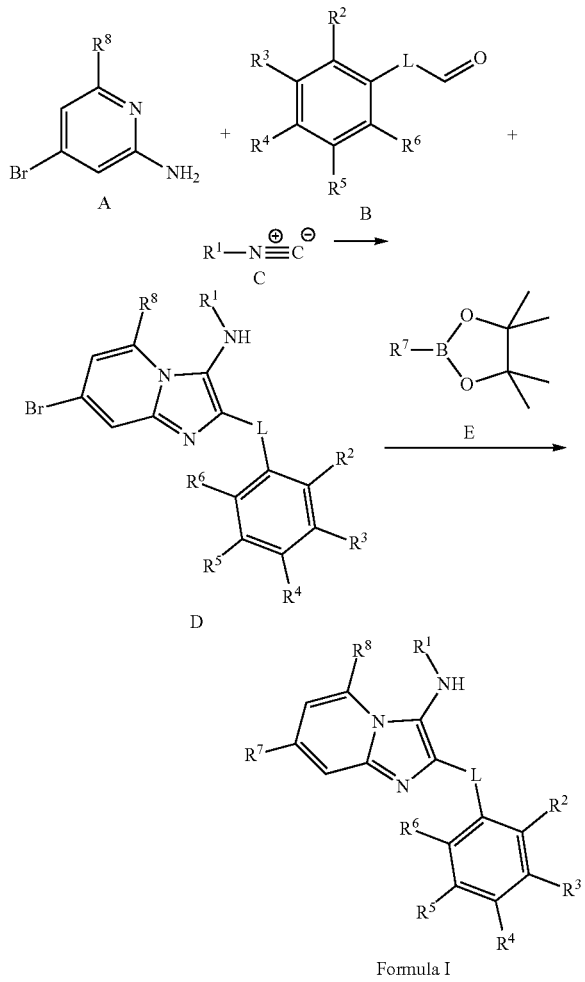

Formula I

Specifically, the synthesis of compounds described herein was accomplished in two-steps: Groebke-Blackburn-Bienayme (GBB) multicomponent reaction (MCR) followed by Suzuki coupling. GBB MCR was first reported in 1998 by three independent research groups, Groebke, Blackburn and Bienayme (a) K. Groebke, L. Weber, F. Mehlin, *Synlett* 1998, 6, 661-663; (b) C. Blackburn, B. Guan, P. Fleming, K. Shiosaki, and S. Tsai, *Tetrahedron Lett.* 1998, 39, 3635-3638; (c) H. Bienayme, K. Bouzid, *Angew. Chem., Int. Ed.* 1998, 37, 2234-2237.

For example, the process of preparing a compound of Formula I, or a pharmaceutically acceptable salt thereof, comprises converting a compound of Formula D:

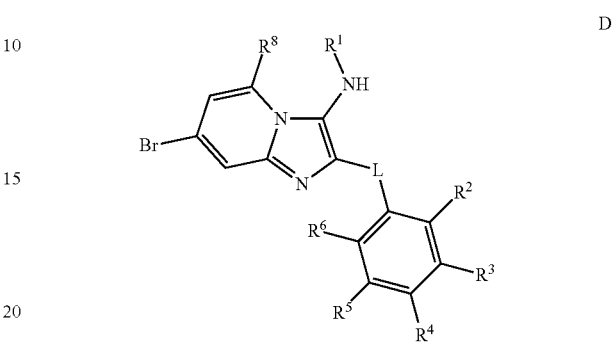

to afford a compound of Formula I, or a pharmaceutically acceptable salt thereof. The process can further include a boronic acid (e.g., 3,5-dimethylisoxazole-4-boronic acid pinacol ester), a transition metal catalyst (e.g., a palladium catalyst such as Pd(dppf)Cl$_2$), and an alkali metal carbonate (e.g., K$_2$CO$_3$). In some embodiment, the process is carried out in the presence of a solvent. The solvent can be an ether (e.g., dimethoxyethane), water, or a mixture thereof. The process can further include heating under microwave irradiation at e.g., about 120° C. for e.g., about 40 minutes.

Compound of Formula D or a salt thereof can be prepared by a process comprising reacting a compound of Formula A, a compound of Formula B, and a compound of Formula C:

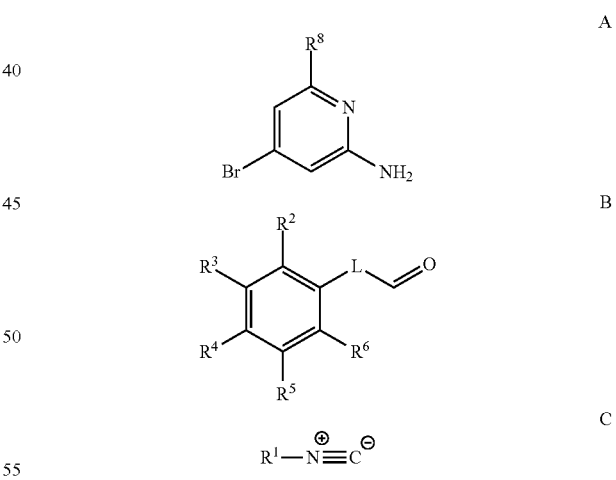

to afford a compound of Formula D or a salt thereof. The process can further include a triflate compound (e.g., Sc(OTf)$_3$). The process can be preformed in the presence of a solvent. The solvent can be a halogenated solvent (e.g., methylene chloride), an alcohol (methanol), or a mixture thereof. The process can further include heating under microwave irradiation at e.g., about 100° C. for e.g., about 40 minutes.

Certain features of the disclosure, for clarity, which described in the context of separate embodiments, can also be provided in combination in a single embodiment. Conversely, various features of the disclosure which are, for brevity, described in the context of a single embodiment, can also be provided separately or in any suitable subcombination.

Definitions of specific functional groups and chemical terms are described in more detail below. The chemical elements are identified in accordance with the Periodic Table of the Elements, CAS version, Handbook of Chemistry and Physics, 75.sup.th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5.sup.th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3.sup.rd Edition, Cambridge University Press, Cambridge, 1987.

At various places in the present disclosure, substituents of compounds are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present disclosure, various aryl, heteroaryl, cycloalkyl, and heterocycloalkyl rings are described. Unless otherwise specified, these rings can be attached to the rest of the molecule at any ring member as permitted by valency. For example, the term "a pyridine ring" may refer to a pyridin-2-yl, pyridin-3-yl, or pyridin-4-yl ring.

The term "n-membered" where n is an integer is used herein to describe the number of ring-forming atoms in a group where the number of ring-forming atoms is n.

When a variable for compounds provided herein appears more than once, the variable can be a different moiety independently selected from the group defining the variable. For example, where a formula is described as having two R groups that are simultaneously present on the same compound, the two R groups can represent different moieties independently selected from the group defined for R.

The term "alkyl" as used herein includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms. In some embodiments, an alkenyl group has 2 to 8 carbon atoms. In some embodiments, an alkenyl group has 2 to 7 carbon atoms. In some embodiments, an alkenyl group has 2 to 6 carbon atoms. In some embodiments, an alkenyl group has 2 to 5 carbon atoms. In some embodiments, an alkenyl group has 2 to 4 carbon atoms. In some embodiments, an alkenyl group has 2 to 3 carbon atoms. In some embodiments, an alkenyl group has 2 carbon atoms. The one or more carbon carbon double bonds can be internal (such as in 2-butenyl) or terminal (such as in 1-butenyl). Examples of alkenyl groups include ethenyl, 1-propenyl, 2-propenyl, 2-butenyl, butadienyl, pentenyl, pentadienyl, hexenyl, heptenyl, octenyl, octatrienyl, and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-8}$ alkenyl. In certain embodiments, the alkenyl group is substituted $C_{2-4}$ alkenyl.

"Alkynyl" refers to a radical of a straight-chain or branched hydrocarbon group having from 2 to 20 carbon atoms, one or more carbon-carbon triple bonds, and optionally one or more double bonds. In some embodiments, an alkynyl group has 2 to 10 carbon atoms. In some embodiments, an alkynyl group has 2 to 9 carbon atoms. In some embodiments, an alkynyl group has 2 to 8 carbon atoms. In some embodiments, an alkynyl group has 2 to 7 carbon atoms. In some embodiments, an alkynyl group has 2 to 6 carbon atoms. In some embodiments, an alkynyl group has 2 to 5 carbon atoms. In some embodiments, an alkynyl group has 2 to 4 carbon atoms. In some embodiments, an alkynyl group has 2 to 3 carbon atoms. In some embodiments, an alkynyl group has 2 carbon atoms. The one or more carbon-carbon triple bonds can be internal (such as in 2-butynyl) or terminal (such as in 1-butynyl). Examples include, without limitation, ethynyl, 1-propynyl, 2-propynyl, 1-butynyl, 2-butynyl, pentynyl, hexynyl, heptynyl, octynyl, and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-8}$ alkynyl. In certain embodiments, the alkynyl group is substituted $C_{2-4}$ alkynyl.

As used herein, "halo" refers to halogen includes fluoro, chloro, bromo, and iodo. In certain embodiments, halo is fluoro or chloro.

As used herein, "haloalkyl" refers to branched or straight-chain saturated hydrocarbon groups substituted with one or more halogen, which may either be the same or different.

Examples of haloalkyl groups include trifluoromethyl, difluoromethyl, pentafluoroethyl, trichloromethyl, etc.

As used herein, "alkoxy" refers to an alkyl group attached through an oxygen atom (—O-alkyl). Examples of alkoxy groups include methoxy, ethoxy, propoxy, t-butoxy, etc.

As used herein, "cycloalkyl" refers to a non-aromatic cyclic hydrocarbon groups. Cycloalkyl groups can include mono- or polycyclic (e.g., fused, bridged, or spiro) ring systems. Cycloalkyl groups can also include one or more aromatic rings fused to the cycloalkyl ring. The ring-forming carbon atoms of a cycloalkyl group can be optionally substituted by oxo. In certain embodiments, the cycloalkyl group is monocyclic. Examples of cycloalkyl groups include cyclopropyl, cyclobutyl, cyclopentyl, cyclohexyl, cycloheptyl, cyclopentenyl, cyclohexenyl, etc.

As used herein, "heterocycloalkyl" refers to a non-aromatic ring, which has at least one heteroatom ring member independently selected from nitrogen, sulfur, and oxygen. Heterocycloalkyl groups can include mono- or polycyclic (e.g., fused, bridged, or spiro) ring systems. Heterocycloalkyl also includes one or more aromatic rings fused to the non-aromatic heterocycloalkyl ring. The ring-forming carbon atoms of a heterocycloalkyl group can be optionally substituted by oxo. The ring-forming heteroatoms of the heterocycloalkyl group can be oxidized to form an N-oxide or a sulfonyl group. Examples of heterocycloalkyl group include morpholine ring, pyrrolidine ring, piperazine ring, piperidine ring, tetrahydropyran ring, tetrahyropyridine, azetidine ring, tetrahydrofuran, etc.

As used herein, "aryl" refers to a monocyclic or polycyclic aromatic hydrocarbon rings. Examples of aryl include phenyl and naphthyl, etc.

As used herein, "heteroaryl" refers to a monocyclic or polycyclic aromatic hydrocarbon ring with one or more heteroatom ring members independently selected from nitrogen, sulfur and oxygen. Examples of heteroaryl include pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, etc. The ring-forming carbon atoms of a heteroaryl group can be optionally substituted by oxo; the ring-forming heteroatoms of the heteroaryl group can be oxidized to form an N-oxide or a sulfonyl group, provided the aromaticity of the ring is preserved.

The compounds provided herein can include one or more isotopes. Isotopes include those atoms having the same atomic number but different mass numbers. For example, isotopes of hydrogen include tritium and deuterium. Isotopes of carbon include $^{13}C$ and $^{14}C$. Compounds of presented herein can be substituted with e.g., one or more deuterium atoms.

As used herein, "pharmaceutically acceptable" refers to compounds, materials, compositions, and/or dosage forms which are, within the scope of sound medical judgment, suitable for administration to a human, e.g., use in contact with the tissues of human beings and animals without excessive toxicity, irritation, allergic response, or other problem or complication, commensurate with a reasonable benefit/risk ratio.

As used herein, "salt" refer compound that is modified by making acid or base salts thereof. The term "pharmaceutically acceptable salts" refers to salts of the compounds provided herein that are suitable for administration to a human or animals. Examples of salts e.g., pharmaceutically acceptable salts, include mineral or organic acid salts of basic residues such as amines; alkali or organic salts of acidic residues such as carboxylic acids; and the like. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish. A "patient" refers to a human subject in need of treatment of a disease.

The terms "administer," "administering," or "administration" refers to implanting, absorbing, ingesting, injecting, inhaling, or otherwise introducing an inventive compound, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment. An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical Formulation and Administration

Provided herein are pharmaceutical compositions comprising a compound described herein, or a pharmaceutically acceptable salt thereof, and at least one pharmaceutically acceptable excipient. The excipient are "acceptable" or "pharmaceutically acceptable" in that they are compatible with the other ingredients of the formulations and not harmful to the recipient. Some examples of suitable excipients and carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

A composition described herein should be formulated to be compatible with its intended route of administration. Examples of routes of administration include oral, parenteral, for example, intravenous, intradermal, inhalation, transdermal (topical), transmucosal, and rectal administration. In some embodiments, the route of administration is oral. In some embodiments, the route of administration is parenteral.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Formulations can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Compositions can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). Suitable carriers include physiological saline, bacteriostatic water, Cremophor ELTM (BASF, Parsippany, N.J.) or phosphate buffered saline (PBS).

Compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals. The compositions can be formulated in a unit dosage form, each dosage containing from about 1 to about 1000 mg, more usually about 10 to about 500 mg, of the compound provided herein.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease associated with CPB in a subject in need thereof, in preventing a disease associated CBP in a subject in need thereof, in reducing the risk to have a disease associated with CBP a subject in need thereof, or in inhibiting the activity of CBP in a subject or cell. It will also be appreciated that the therapy employed may achieve a desired effect for the same disorder, and/or it may achieve different effects. In certain embodiments, an inventive pharmaceutical composition including a compound of the invention and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, anti-diabetic agents, anti-allergic agents, and pain-relieving agents. In certain embodiments, the additional pharmaceutical agent is an inhibitor of CBP. In certain embodiments, the additional pharmaceutical agent is selected from the group consisting of (+)-JQ1, (−)-JQ1, I-BET, and PFI-1. See, e.g., international PCT patent application publication, WO 2011/143669. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the inventive compounds or pharmaceutical compositions can be administered in combination with an anti-cancer therapy including, but not limited to, surgery, radiation therapy, and chemotherapy.

Uses of the Compounds

The compounds provided herein can be useful in treating diseases or disorders associated with CBP, wherein said method comprises administering to a subject in need thereof a therapeutically effective amount of a compound described herein, or a pharmaceutically acceptable salt thereof. In some embodiments, provided herein are methods of inhibiting CBP activity, wherein said method comprise contacting a compound described herein, or a pharmaceutically acceptable salt thereof, with CBP. In some embodiments, contacting comprises administering the compound to a subject.

Compounds in the literature that bind CBP with $K_d$ values in the nanomolar range typically also bind proteins other than CBP such as BRD4, which is an off-target binding partner for the CBP inhibitors. These known compounds are not selective for CBP and thus, can cause unwanted, off-target effects in subjects. The compounds described herein are selective for CBP. The activity and selectivity of the compounds provided can be measured using in vitro binding assays such as AlphaScreen in vitro binding assays. In some embodiments, the compounds provided herein are 2 fold, 3 fold, 4 fold, 5 fold, 10 fold, 15 fold, 20 fold, 25 fold, 50 fold, 75 fold, 100 fold, 150 fold, 200 fold, 250 fold, 300 fold, 350 fold, 400 fold, 450 fold, 500 fold, 1000 fold, etc. more selective for CBP than BRD4 as measured by the AlphaScreen in vitro binding assay described herein. In some embodiments, the compounds provided herein are 2 fold more selective for CBP than BRD4. In some embodiments, the compounds provided herein are 5 fold more selective for CBP than BRD4. In some embodiments, the compounds provided herein are 10 fold more selective for CBP than BRD4. In some embodiments, the compounds provided herein are 20 fold more selective for CBP than BRD4. In some embodiments, the compounds provided herein are 50 fold more selective for CBP than BRD4. In some embodiments, the compounds provided herein are 75 fold more selective for CBP than BRD4. In some embodiments, the compounds provided herein are 100 fold more selective for CBP than BRD4.

In some embodiments, provided herein are methods for treating cancer in a subject, wherein said method comprises administering to the subject a therapeutically effective amount of the compound described herein, or a pharmaceutically acceptable salt thereof. The term "cancer" refers to a malignant neoplasm (Stedman's Medical Dictionary, 25th ed.; Hensyl ed.; Williams & Wilkins: Philadelphia, 1990).

Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In some embodiments, the cancer is bone cancer, pancreatic cancer, skin cancer, cancer of the head or neck, melanoma, uterine cancer, ovarian cancer, rectal cancer, cancer of the anal region, stomach cancer, testicular cancer, uterine cancer, carcinoma, solid tumors, lymphoma, cancer of the bladder, cancer of the kidney, acute lymphoblastic leukemia (ALL), acute myelogenous leukemia (AML), chronic lymphocytic leukemia (CLL), chronic myelogenous leukemia (CML), DLBCL, mantle cell lymphoma, non-Hodgkin lymphoma, or Hodgkin lymphoma.

In some embodiments, provided herein are methods for treating neurodegenerative disease in a subject, wherein said method comprises administering to the subject a therapeutically effective amount of the compound described herein, or a pharmaceutically acceptable salt thereof.

In some embodiments, provided herein are methods for treating angiogenesis in a subject, wherein said method comprises administering to the subject a therapeutically effective amount of the compound described herein, or a pharmaceutically acceptable salt thereof.

In some embodiments, provided herein are methods for treating an inflammatory disease in a subject, wherein said method comprises administering to the subject a therapeutically effective amount of the compound described herein, or a pharmaceutically acceptable salt thereof.

In some embodiments, provided herein are methods for treating an immune disease in a subject, wherein said method comprises administering to the subject a therapeutically effective amount of the compound described herein, or a pharmaceutically acceptable salt thereof.

Kits

The present disclosure also provides kits, e.g., pharmaceutical kits useful in live-cell imaging and treatment of disease associated with iron dyshomoestasis, which include one or more containers containing a composition comprising an effective amount of a compound of the provided herein. The kits can further include one or more of various conventional kit components, e.g., containers with one or more carriers, additional containers, etc. The kit can also include instructions (e.g., as inserts or as labels) indicating quantities of the components to be administered, guidelines for administration, and/or guidelines for mixing the components.

EXAMPLES

The invention is further described in the following examples, which do not limit the scope of the invention described in the claims.

General Information

The following materials and methods were used in the Examples set forth herein.

Chemicals and solvents were purchased from commercial suppliers and used as received. All the compounds used for biological assay were >95% pure as determined by NMR and liquid-chromatography coupled to mass spectrometry (LC-MS) as described below.

$^1$H NMR (400 MHz) and $^{13}$C NMR spectra (101 MHz) were recorded on Agilent NMR spectrometers. The chemical shifts were reported in parts per million (ppm), and the residual solvent peak was used as an internal reference: proton (chloroform δ 7.26) and carbon (chloroform δ 77.0). Multiplicities were indicated as follows: s (singlet), d (doublet), t (triplet), q (quartet), m (multiplet), dd (doublet of doublet), br s (broad singlet). Coupling constants were reported in hertz (Hz).

LC-MS was performed on an Agilent 2100 LC with a 6130 quadrupole MS spectrometer, and a C18 column (5.0 m, 6.0×50 mm) was used for separation. The mobile phases were methanol (MeOH) and water; both containing 0.01% trifluoroacetic acid. A linear gradient of 50:50 (v/v) MeOH/H$_2$O to 100% MeOH was used over 7.0 min at a flow rate of 0.7 mL/min. The chromatograms were detected at UV wavelengths 210, 254, and 365 nm. Low resolution mass spectra were recorded in APCI (atmospheric pressure chemical ionization). The microwave reactions were performed on a Biotage Initiator 8 system.

Flash chromatography separation was performed on YAMAZEN AI-580 system with Agela silica gel (12 or 20 g, 230-400 m mesh) cartridges.

In some instances, reaction intermediates and final products were purified using Agela HP-100 pre-LC system with a Venusil PrepG C18 column (10 m, 120 Å, 21.2 mm×250 mm.

Example 1. Synthesis of Compounds that Potentially Selectively Inhibit CBP

In this Example chemical approaches employing atom- and step economy were utilized to synthesize novel compounds that selectively bind CBPs and have reduced off-target binding to BRD4, a representative off-target protein. See Scheme 2 below:

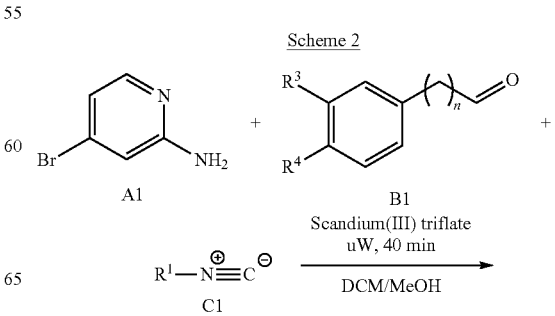

-continued

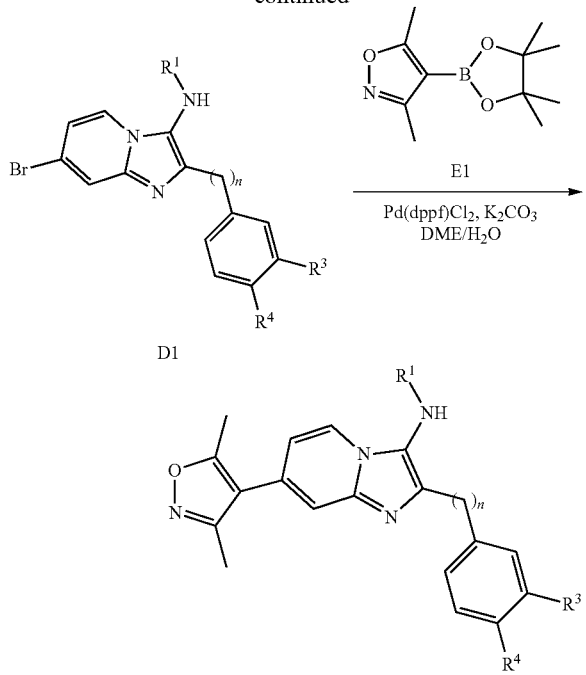

R³ and R⁴ = H, Cl or OMe n = 0, 1, 2, or 3

Herein a two-step synthesis of imidazo[1,2-a]pyridine scaffold based CBP inhibitors is reported. Specifically, a Groebke-Blackburn-Bienayme multicomponent reaction (K. Groebke et al. 6, 661-663 (1998); C. Blackburn et al. Tetrahedron Lett. 39, 3635-3638 (1998); H. Bienayme and K. Bouzid. Angew. Chem., Int. Ed. 37, 2234-2237 (1998)) was performed followed by suzuki coupling. In this study an imidazo[1,2-a]pyridine scaffold was used, with substituent groups around the imidazo[1,2-a]pyridine scaffold varied by use of different aldehydes, isocyanides and also warheads as acetylysine mimic; 3,5-dimethylisoxazole, 3-methyl-2H-indazole, 3-methyl-3a,7a-dihydrobenzo[d]isoxazole and 3-methyl-3,4-dihydroquinazolin-2(1H)-one to get a collection of compounds.

The synthesis of imidazo[1,2-a]pyridine scaffold based CBP inhibitors was performed in two steps: (1) Groebke-Blackburn-Bienayme multicomponent reaction (N. H. Theodoulou et al., Curr. Opin. Chem. Biol. 33, 58-66 (2016)) followed by (2) Suzuki coupling.

For the Groebke-Blackburn-Bienayme reaction, a sealed vial (5 mL microwave tube) was charged with 2-amino-4-bromopyridine (0.173 mmol, 1.0 equiv), aldehyde (0.208 mmol, 1.2 equiv), isocyanide (0.173 mmol, 1.0 equiv), and Sc(OTf)$_3$ (0.014 mmol, 0.08 equiv.) in 2 mL of 3:1 CH$_2$Cl$_2$/MeOH and heated under microwave irradiation at 100° C. for 40 min. The reaction mixture was concentrated and purified using flash chromatography. The desired product was eluted with 15% EtOAc/hexane, to give a yellow solid (65-75 mg, 95-97%). The aforementioned purified product was utilized as reactant in a Suzuki coupling reaction.

A sealed reaction vial (5 mL microwave tube) was charged with Groebke-Blackburn-Bienayme multicomponent reaction product (0.07 mmol, 1 equiv), 3,5-dimethylisoxazole-4-boronic acid pinacol ester (0.084 mmol, 1.2 equiv.), Pd(dppf)Cl$_2$.CH$_2$Cl$_2$ (0.0056 mmol, 0.08 equiv.), and K$_2$CO$_3$ (0.14 mmol, 2.0 equiv.) in 2 mL of 2:1 DME/H$_2$O was heated under microwave irradiation at 120° C. for 40 min. The mixture was filtered on Celite and washed with EtOAc (4 mL). Concentration of the organic phase gave a crude product which was purified by flash chromatography using 20% EtOAc/hexane to give a yellow solid (55-64 mg, 85-91%). The purity of the compounds (chemical structures are depicted in FIGS. 3A-3E, FIGS. 5A-5U, and FIGS. 7A-7K) was assessed by $^1$H NMR and $^{13}$C NMR; results are included below.

N-((3s,5s,7s)-adamantan-1-yl)-2-(4-methoxyphenyl)-5,7-dimethylimidazo[1,2-a]pyridin-3-amine (Compound 1, 91% yield). $^1$H NMR (400 MHz, CDCl$_3$) δ 7.76-7.69 (m, 2H), 7.15 (s, 1H), 6.97-6.93 (m, 2H), 6.27 (s, 1H), 3.86 (s, 3H), 2.93 (s, 3H), 2.32 (s, 3H), 1.52-1.40 (m, 6H), 1.35-1.25 (m, 2H), 0.97-0.87 (m, 2H). $^{13}$C NMR (101 MHz, CDCl$_3$) δ 158.76, 143.62, 136.03, 134.63, 129.72, 128.69, 116.43, 113.96, 113.60, 56.62, 55.57, 55.23, 42.97, 36.25, 29.64, 20.96, 20.89.

N-cyclohexyl-7-(3,5-dimethylisoxazol-4-yl)-2-phenethylimidazo[1,2-a]pyridin-3-amine (Compound 5, 88% yield). $^1$H NMR (400 MHz, CDCl$_3$) δ 8.22 (dd, J=7.1, 0.9 Hz, 1H), 7.37 (dd, J=1.7, 0.9 Hz, 1H), 7.29 (dd, J=7.9, 6.7 Hz, 2H), 7.23-7.19 (m, 3H), 6.64 (dd, J=7.1, 1.7 Hz, 1H), 3.14-3.04 (m, 4H), 2.48 (s, 3H), 2.35 (s, 3H), 1.66 (d, J=2.8 Hz, 6H), 1.59 (d, J=22.3 Hz, 4H), 0.91 (dt, J=9.7, 7.3 Hz, 1H). $^{13}$C NMR (101 MHz, CDCl$_3$) δ 165.70, 158.51, 142.13, 141.76, 141.19, 128.57, 128.41, 125.98, 125.67, 123.53, 122.93, 116.10, 115.25, 111.80, 68.12, 55.40, 43.90, 36.17, 30.39, 29.64, 24.86, 11.84, 11.04.

2-(4-methoxyphenyl)-5,7-dimethyl-N-(2,4,4-trimethylpentan-2-yl)imidazo[1,2-a]pyridin-3-amine (Compound 8, 92% yield). $^1$H NMR (400 MHz, CDCl$_3$) δ 7.70-7.68 (m, 1H), 7.67 (d, J=2.2 Hz, 1H), 7.15 (s, 1H), 6.98-6.95 (m, 2H), 6.28 (s, 1H), 3.85 (s, 3H), 2.91 (s, 3H), 2.31 (s, 3H), 1.45 (s, 2H), 0.95 (s, 9H), 0.77 (s, 6H). $^{13}$C NMR (101 MHz, CDCl$_3$) δ 158.88, 143.68, 135.93, 134.64, 130.86, 129.87, 128.77, 124.29, 116.44, 113.68, 60.55, 56.22, 55.26, 31.83, 30.33, 28.33, 22.98, 20.77, 14.05.

7-(3,5-dimethylisoxazol-4-yl)-2-phenethyl-N-(2,4,4-trimethylpentan-2-yl)imidazo[1,2-a]pyridin-3-amine (Compound 13, 89%). $^1$H NMR (400 MHz, CDCl$_3$) δ 8.17 (dd, J=7.1, 1.0 Hz, 1H), 7.36 (dd, J=1.7, 0.9 Hz, 1H), 7.32-7.27 (m, 2H), 7.24-7.17 (m, 3H), 6.65 (dd, J=7.1, 1.7 Hz, 1H), 3.13-3.05 (m, 4H), 2.48 (s, 3H), 2.34 (s, 3H), 1.59 (s, 2H), 1.14 (s, 6H), 1.07 (s, 9H). $^{13}$C NMR (101 MHz, CDCl$_3$) δ 165.72, 158.52, 142.09, 141.86, 141.32, 128.53, 128.44, 126.02, 125.72, 123.51, 116.21, 115.23, 111.86, 59.50, 56.77, 35.84, 31.94, 31.78, 30.54, 29.22, 11.84, 11.04.

N-(tert-butyl)-7-(3,5-dimethylisoxazol-4-yl)-2-phenethylimidazo[1,2-a]pyridin-3-amine (Compound 14, 84% yield). $^1$H NMR (400 MHz, CDCl$_3$) δ 8.17 (dd, J=7.1, 1.0 Hz, 1H), 7.37 (dd, J=1.7, 0.9 Hz, 1H), 7.31-7.27 (m, 2H), 7.22-7.18 (m, 3H), 6.64 (dd, J=7.1, 1.7 Hz, 1H), 3.10-3.07 (m, 4H), 2.48 (s, 3H), 2.34 (s, 3H), 1.25 (s, 6H), 1.15 (s, 9H). $^{13}$C NMR (101 MHz, CDCl$_3$) δ 165.73, 158.51, 142.09, 141.81, 141.11, 128.55, 128.44, 126.01, 125.80, 123.44, 116.18, 111.88, 110.78, 55.37, 35.82, 30.94, 30.29, 24.85, 11.83, 11.03.

N-((3s,5s,7s)-adamantan-1-yl)-7-(3,5-dimethylisoxazol-4-yl)-2-(4-methoxyphenethyl)imidazo[1,2-a]pyridine-3-amine (Compound 16, 81% yield).). $^1$H NMR (400 MHz, CDCl$_3$) δ 8.23 (dd, J=7.1, 0.9 Hz, 1H), 7.36 (dd, J=1.8, 1.0 Hz, 1H), 7.14-7.10 (m, 2H), 6.85-6.81 (m, 2H), 6.64 (dd, J=7.1, 1.7 Hz, 1H), 3.79 (s, 3H), 2.48 (s, 3H), 2.35 (s, 3H), 1.66 (d, J=2.9 Hz, 7H), 1.63 (d, J=8.7 Hz, 6H). $^{13}$C NMR (101 MHz, CDCl$_3$) δ 158.54, 157.88, 134.22, 129.48, 123.54, 116.11, 113.83, 111.82, 55.44, 55.29, 43.92, 43.87, 36.18, 34.88, 30.62, 29.66, 11.87, 11.07.

N-cyclohexyl-7-(3,5-dimethylisoxazol-4-yl)-2-(4-methoxyphenethyl)imidazo[1,2-a]pyridin-3-amine (Compound 18, 90% yield)). $^1$H NMR (400 MHz, CDCl$_3$) δ 8.03 (dd, J=7.0, 0.9 Hz, 1H), 7.36 (dd, J=1.7, 0.9 Hz, 1H), 7.17-7.03 (m, 2H), 6.88-6.73 (m, 2H), 6.64 (dd, J=7.0, 1.7 Hz, 1H), 3.78 (s, 3H), 3.01 (dtd, J=11.8, 5.9, 1.7 Hz, 4H), 2.47 (s, 3H), 2.33 (s, 2H), 1.80-1.67 (m, 4H), 1.60 (s, 1H), 1.36-1.29 (m, 1H), 1.28-1.07 (m, 5H). $^{13}$C NMR (101 MHz, CDCl$_3$) δ 165.68, 158.53, 157.89, 141.21, 139.34, 134.13, 129.47, 125.36, 122.62, 116.37, 115.31, 113.81, 112.15, 57.20, 55.26, 34.91, 34.22, 30.21, 25.72, 24.83, 11.81, 11.01.

7-(3,5-dimethylisoxazol-4-yl)-N-isopropyl-2-(4-methoxyphenethyl)imidazo[1,2-a]pyridin-3-amine (Compound 19, 87% yield). $^1$H NMR (400 MHz, CDCl$_3$) δ 8.25 (d, J=7.1 Hz, 1H), 8.16 (s, 1H), 7.11 (dd, J=7.0, 1.3 Hz, 1H), 7.08-7.04 (m, 2H), 6.83-6.79 (m, 2H), 4.27-4.15 (m, 1H), 3.78 (s, 3H), 3.15 (q, J=8.2, 7.6 Hz, 2H), 3.09 (dd, J=9.6, 6.4 Hz, 2H), 2.55 (s, 3H), 2.38 (s, 3H), 1.05 (s, 3H), 1.03 (s, 3H). $^{13}$C NMR (101 MHz, CDCl$_3$) δ 167.47, 158.35, 157.86, 137.33, 133.98, 132.14, 129.59, 126.49, 123.42, 116.40, 114.13, 113.52, 112.59, 55.32, 49.71, 38.68, 33.93, 27.25, 23.22, 12.12, 11.09.

2-(3-chloro-4-methoxyphenethyl)-N-cyclohexyl-7-(3,5-dimethylisoxazol-4-yl)imidazo[1,2-a]pyridin-3-amine (Compound 21, 85% yield)$^1$H NMR (400 MHz, CDCl$_3$) δ 8.05 (dd, J=7.0, 1.0 Hz, 1H), 7.36 (dd, J=1.7, 0.9 Hz, 1H), 7.23 (d, J=2.2 Hz, 1H), 7.04 (dd, J=8.3, 2.2 Hz, 1H), 6.83 (d, J=8.4 Hz, 1H), 6.66 (dd, J=7.0, 1.7 Hz, 1H), 3.87 (s, 3H), 3.08-2.97 (m, 4H), 2.66-2.52 (m, 1H), 2.48 (s, 3H), 2.34 (s, 3H), 1.80-1.69 (m, 4H), 1.28-1.11 (m, 6H). $^{13}$C NMR (101 MHz, CDCl$_3$) δ 165.70, 158.50, 153.24, 141.27, 138.97, 135.23, 130.19, 127.75, 125.53, 122.64, 122.07, 116.37, 115.27, 112.23, 112.00, 57.24, 56.15, 34.47, 34.23, 29.74, 25.70, 24.81, 11.80, 11.00.

N-cyclohexyl-7-(3,5-dimethylisoxazol-4-yl)-2-(4-ethoxyphenethyl)imidazo[1,2-a]pyridin-3-amine (Compound 22, 90% yield). $^1$H NMR (400 MHz, CDCl$_3$) δ 8.05 (dd, J=7.0, 1.0 Hz, 1H), 7.37 (dd, J=1.7, 0.9 Hz, 1H), 7.11-7.07 (m, 2H), 6.83-6.78 (m, 2H), 6.66 (dd, J=7.0, 1.7 Hz, 1H), 4.01 (q, J=7.0 Hz, 2H), 3.07-2.97 (m, 4H), 2.74-2.62 (m, 1H), 2.47 (s, 3H), 2.34 (s, 3H), 1.80-1.68 (m, 4H), 1.40 (t, J=7.0 Hz, 3H), 1.26-1.12 (m, 6H). $^{13}$C NMR (101 MHz, CDCl$_3$) δ 165.68, 158.51, 157.24, 141.16, 139.26, 133.95, 129.44, 125.41, 125.39, 122.62, 116.31, 115.29, 114.41, 112.18, 63.39, 57.19, 34.92, 34.20, 30.16, 25.71, 24.81, 14.88, 11.80, 11.00.

N-cyclohexyl-7-(3,5-dimethylisoxazol-4-yl)-2-(3-(4-methoxyphenyl)propyl)imidazo[1,2-a]pyridin-3-amine (Compound 27, 87% yield). $^1$H NMR (400 MHz, CDCl$_3$) δ 8.06 (dd, J=7.0, 1.0 Hz, 1H), 7.35 (dd, J=1.7, 0.9 Hz, 1H), 7.15-7.11 (m, 2H), 6.86-6.81 (m, 2H), 6.66 (dd, J=7.0, 1.7 Hz, 1H), 3.79 (s, 3H), 2.79 (q, J=4.0, 3.5 Hz, 1H), 2.76-2.70 (m, 2H), 2.67 (t, J=7.5 Hz, 2H), 2.46 (s, 3H), 2.32 (s, 3H), 2.11 (tt, J=8.8, 6.8 Hz, 2H), 1.84-1.71 (m, 4H), 1.24 (s, 2H), 1.20-1.14 (m, 4H). $^{13}$C NMR (101 MHz, CDCl$_3$) δ 165.69, 158.54, 157.71, 141.17, 139.92, 134.13, 129.37, 125.31, 124.95, 122.53, 116.39, 115.33, 113.70, 112.20, 57.21, 55.26, 34.57, 34.22, 30.94, 26.46, 25.74, 24.85, 11.78, 10.99.

7-(3,5-dimethylisoxazol-4-yl)-2-(4-methoxyphenethyl)-N-(2,4,4-trimethylpentan-2-yl)imidazo[1,2-a]pyridin-3-amine (Compound 28, 81% yield). $^1$H NMR (400 MHz, CDCl$_3$) δ 8.18 (d, J=7.0 Hz, 1H), 7.38 (s, 1H), 7.11-7.07 (m, 2H), 6.85-6.80 (m, 2H), 6.65 (dd, J=7.1, 1.6 Hz, 1H), 3.79 (s, 3H), 3.04 (s, 3H), 2.48 (s, 3H), 2.35 (s, 3H), 1.25 (s, 2H), 1.14 (s, 6H), 1.08 (s, 9H). $^{13}$C NMR (101 MHz, cdcl$_3$) δ 165.74, 158.50, 157.87, 134.08, 129.43, 123.83, 123.51, 116.11, 115.20, 113.82, 111.92, 59.50, 56.77, 55.21, 34.92, 31.93, 31.86, 31.77, 30.73, 29.23, 24.85, 11.85, 11.04.

7-(3,5-dimethylisoxazol-4-yl)-2-(4-ethoxyphenethyl)-N-(2,4,4-trimethylpentan-2-yl)imidazo[1,2-a]pyridin-3-amine (Compound 29, 90% yield). $^1$H NMR (400 MHz, CDCl$_3$) δ 8.17 (dd, J=7.1, 0.9 Hz, 1H), 7.37 (dd, J=1.7, 0.9 Hz, 1H), 7.12-7.03 (m, 2H), 6.86-6.77 (m, 2H), 6.65 (dd, J=7.1, 1.7 Hz, 1H), 4.01 (q, J=6.9 Hz, 2H), 3.03 (s, 4H), 2.48 (s, 3H), 2.37 (s, OH), 2.34 (s, 3H), 1.58 (s, 2H), 1.41 (t, J=7.0 Hz, 3H), 1.13 (s, 6H), 1.07 (s, 9H). $^{13}$C NMR (101 MHz, CDCl$_3$) δ 165.75, 158.53, 157.26, 141.77, 133.95, 129.43, 123.87, 123.53, 116.13, 115.22, 114.42, 111.91, 63.36, 59.51, 56.78, 34.96, 31.94, 31.79, 30.77, 29.24, 14.90, 11.86, 11.05.

Example 2. Determination of Binding Affinity of Synthesized Compounds for CBP and BRD4 Using In Vitro AlphaScreen Assay To determine the binding selectivity of compounds provided, AlphaScreen in vitro binding assays were performed with either CBP or BRD4.

Assays were performed with minor modifications from the manufacturer's protocol (Perkin Elmer, USA). All reagents were diluted in AlphaScreen™ buffer (50 mM HEPES, 150 mM NaCl, 0.01% v/v Tween-20, 0.1% w/v BSA, pH 7.4). After addition of Alpha beads to master solutions, all subsequent steps were performed under low light conditions. A 2× solution of components with final concentrations of His-BRD4(1) at 20 nM or His-CBP at 50 nM, Ni-coated Acceptor bead at 10 μg/ml, and biotinylated-JQ1 at 10 nM or biotinylated peptide at 100 nM was added in 10 μL to 384-well plates (AlphaPlate-384, PerkinElmer) using an EL406 liquid handler (Biotek, USA). Plates were spun down at 1000 rpm. A 10-point 1: √sqrt(10) serial dilution of compounds in DMSO was prepared at 200× the final concentration. 100 nL of compound from these stock plates were added by pin transfer using a Janus Workstation (PerkinElmer). A 2× solution of streptavidin-coated donor beads with a final concentration of 10 μg/ml was added in a 10 μL volume. The plates were spun down again at 1000 rpm and sealed with foil to prevent light exposure and evaporation. The plates were then incubated at room temperature for 1 hour and read on an Envision 2104 (PerkinElmer) using the manufacturer's protocol. IC$_{50}$ values were calculated using a 4-parameter logistic curve in Prism 6 (GraphPad Software, USA) after normalization to DMSO-treated negative control wells.

TABLE 1

| | IC$_{50}$ values | | |
|---|---|---|---|
| | IC$_{50}$ (μM)[a] | | Selectivity |
| Compound | CBP | BRD4 | Value[b] |
| JQ1 | >50 | 0.069[c] | |
| CBP | 0.042[c] | 8.231[c] | |
| 1 | 16.09 | >50 | >3 |
| 2 | 2.216 | >50 | >23 |
| 3 | 14.19 | >50 | >4 |
| 4 | 7.828 | >50 | >6 |
| 5 | 0.718 | 7.433 | 10 |
| 6 | 0.507 | 3.38 | 7 |
| 7 | 1.17 | 2.955 | 3 |
| 8 | 16.33 | >50 | >3 |
| 10 | 8.122 | 7.548 | <1 |

TABLE 1-continued

IC$_{50}$ values

| Compound | IC$_{50}$ (μM)[a] CBP | IC$_{50}$ (μM)[a] BRD4 | Selectivity Value[b] |
|---|---|---|---|
| 11 | 8.024 | 0.510 | <1 |
| 12 | >50 | 3.027 | <1 |
| 13 | 1.88 | 2.773 | 1 |
| 14 | 0.956 | 5.637 | 6 |
| 15 | 1.553 | 4.218 | 3 |
| 16 | 0.923 | 7.11 | 8 |
| 17 | 0.464 | 3.422 | 7 |
| 18 | 0.159 | 6.591 | 41 |
| 19 | 0.296 | 10.09 | 34 |
| 20 | 2.338 | >50 | >21 |
| 21 | 0.072 | 5.193 | 72 |
| 22 | 0.214 | 6.48 | 30 |
| 23 | 0.633 | 17.92 | 28 |
| 24 | 1.924 | 8.469 | 4 |
| 25 | 1.609 | 7.948 | 5 |
| 26 | 6.074 | 11.22 | 2 |
| 27 | 4.95 | 12.33 | 3 |
| 28 | 20.89 | >50 | >2 |
| 29 | 38.49 | >50 | >1 |
| 30 | >50 | >50 | 1 |
| 31 | 2.536 | >50 | 20 |
| 32 | 20.46 | >50 | >2 |
| 33 | 0.759 | 6.219 | 8 |
| 34 | 3.515 | 22.64 | 6 |
| 35 | >50 | >50 | 1 |
| 36 | 0.737 | 8.185 | 11 |
| 37 | 1.575 | 11.010 | 7 |

[a] All IC$_{50}$ values are reported as means of values from at least two determinations. AlphaScreen assay with the isolated CBP or BRD4 bromodomain.
[b] Selectivity value is defined by [BRD4(1) IC$_{50}$ (μM)/CBP IC$_{50}$ (μM)]
[c] Average of three determinations.

What is claimed is:

1. A compound of Formula I:

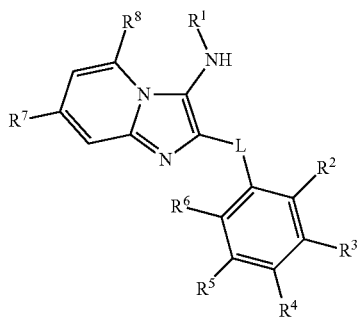

(I)

or a pharmaceutically acceptable salt thereof, wherein:

L is $(CR^aR^b)_n$;

$R^a$ and $R^b$ are each independently selected from H, $C_{1-8}$ alkyl, $C_{2-8}$ alkenyl, and $C_{2-8}$ alkynyl;

n is 0, 1, 2, or 3;

$R^1$ is selected from $C_{1-8}$ alkyl, $C_{2-8}$ alkenyl, $C_{2-8}$ alkynyl, $C_{1-6}$ haloalkyl, C(O)H, C(O)($C_{1-8}$ alkyl), C(O)OH, C(O)O($C_{1-8}$ alkyl), $C_{3-10}$ cycloalkyl, $C_{3-10}$ cycloalkyl-$C_{1-4}$ alkylene, 4-10 membered heterocycloalkyl, 4-10 membered heterocycloalkyl-$C_{1-4}$ alkylene, $C_{6-10}$ aryl, $C_{6-10}$ aryl-$C_{1-4}$ alkylene, 5-10 membered heteroaryl, and 5-10 membered heteroaryl-$C_{1-4}$ alkylene; wherein the 4-10 membered heterocycloalkyl, 4-10 membered heterocycloalkyl-$C_{1-4}$ alkylene, 5-10 membered heteroaryl, and 5-10 membered heteroaryl-$C_{1-4}$ alkylene each has at least one ring-forming carbon atom and 1, 2, 3, or 4 ring-forming heteroatoms independently selected from N, O, and S; wherein the N and S are optionally oxidized; and wherein the $C_{1-8}$ alkyl, $C_{2-8}$ alkenyl, $C_{2-8}$ alkynyl, $C_{3-10}$ cycloalkyl, $C_{3-10}$ cycloalkyl-$C_{1-4}$ alkylene, 4-10 membered heterocycloalkyl, 4-10 membered heterocycloalkyl-$C_{1-4}$ alkylene, $C_{6-10}$ aryl, $C_{6-10}$ aryl-$C_{1-4}$ alkylene, 5-10 membered heteroaryl, and 5-10 membered heteroaryl-$C_{1-4}$ alkylene are each optionally substituted with 1, 2, or 3 substituents selected from halo, C(O)H, C(O)($C_{1-8}$ alkyl), C(O)OH, and C(O)O($C_{1-8}$ alkyl);

$R^2$, $R^3$, $R^4$, $R^5$, and $R^6$ are each independently selected from H, halo, $C_{1-8}$ alkyl, $C_{2-8}$ alkenyl, $C_{2-8}$ alkynyl, $C_{1-8}$ haloalkyl, OH, and O-$C_{1-8}$ alkyl;

$R^7$ is selected from Cy, $C_{2-8}$ alkenyl, and $C_{2-8}$ alkynyl;

$R^8$ is selected from H, $C_{1-8}$ alkyl, $C_{2-8}$ alkenyl, and $C_{2-8}$ alkynyl; and Cy is selected from 4-10 membered heterocycloalkyl and 5-10 membered heteroaryl;

wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; and wherein the 4-10 membered heterocycloalkyl and 5-10 membered heteroaryl are each optionally substituted with 1, 2, 3 or 4 substituents independently selected from oxo, $C_{1-8}$ alkyl, $C_{2-8}$ alkenyl, and $C_{2-8}$ alkynyl.

2. The compound of claim 1, wherein the compound is a compound of Formula II:

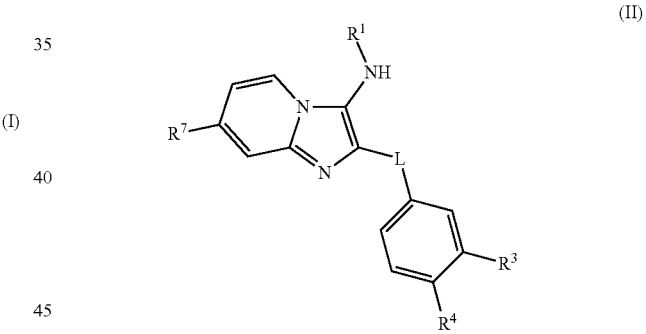

(II)

or a pharmaceutically acceptable salt thereof.

3. The compound of claim 1, wherein the compound is a compound of Formula III:

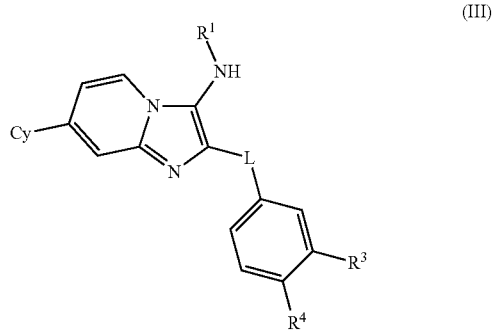

(III)

or a pharmaceutically acceptable salt thereof.

4. The compound of claim 1, wherein the compound is a compound of Formula IV:

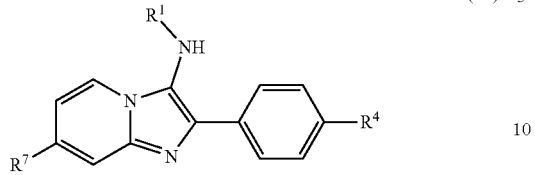

(IV)

or a pharmaceutically acceptable salt thereof.

5. The compound of claim 1, wherein the compound is a compound of Formula V:

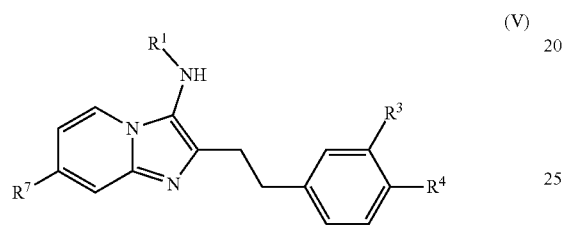

(V)

or a pharmaceutically acceptable salt thereof.

6. The compound of claim 1, wherein n is 0.

7. The compound of claim 1, wherein n is 2.

8. The compound of claim 1, wherein $R^a$ is H.

9. The compound of claim 1, wherein $R^b$ is H.

10. The compound of claim 1, wherein $R^1$ is $C_{1-8}$ alkyl optionally substituted with 1, 2, or 3 substituents selected from halo, C(O)H, C(O)($C_{1-8}$ alkyl), C(O)OH, and C(O)O ($C_{1-8}$ alkyl).

11. The compound of claim 1, wherein $R^1$ is $C_{3-10}$ cycloalkyl.

12. The compound of claim 1, wherein $R^1$ is 4-10 membered heterocycloalkyl-$C_{1-4}$ alkylene.

13. The compound of claim 1, wherein $R^1$ is $C_{6-10}$ aryl or $C_{6-10}$ aryl-$C_{1-4}$ alkylene.

14. The compound of claim 1, wherein $R^2$, $R^3$, $R^4$, $R^5$, and $R^6$ are H.

15. The compound of claim 1, wherein $R^2$, $R^5$, and $R^6$ are each H.

16. The compound of claim 1, wherein $R^3$ is halo, $C_{1-8}$ alkyl, OH, and O-$C_{1-8}$ alkyl.

17. The compound of claim 1, wherein $R^4$ is halo, $C_{1-8}$ alkyl, OH, and O-$C_{1-8}$ alkyl.

18. The compound of claim 1, wherein $R^7$ is Cy.

19. The compound of claim 18, wherein Cy is 5-10 membered heteroaryl optionally substituted with 1, 2, 3 or 4 substituents independently selected from oxo, $C_{1-8}$ alkyl, $C_{2-8}$ alkenyl, and $C_{2-8}$ alkynyl.

20. The compound of claim 18, wherein Cy is isoxazolyl, indazolyl, 3,4-dihydroquinazolin-2(1H)-onyl, or 3a,7a-dihydrobenzo[d]isoxazolyl.

21. The compound of claim 1, wherein $R^8$ is H.

22. The compound of claim 1, wherein the compound is selected from:

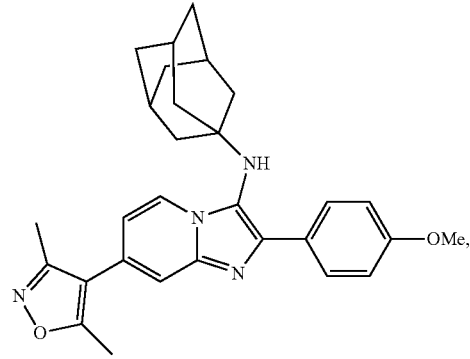

2

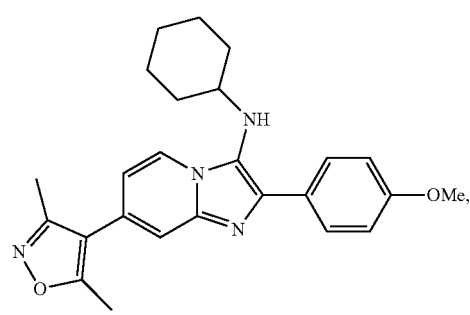

3

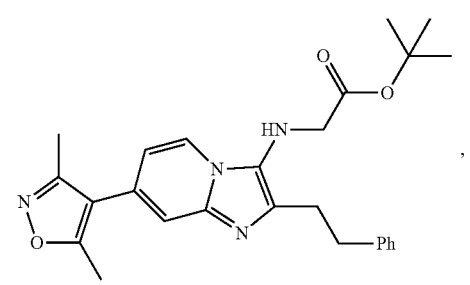

4

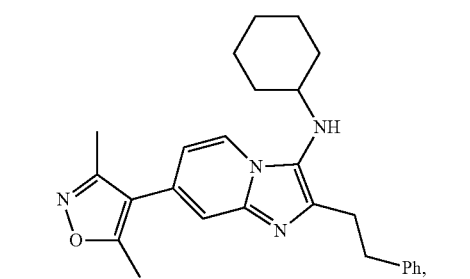

5

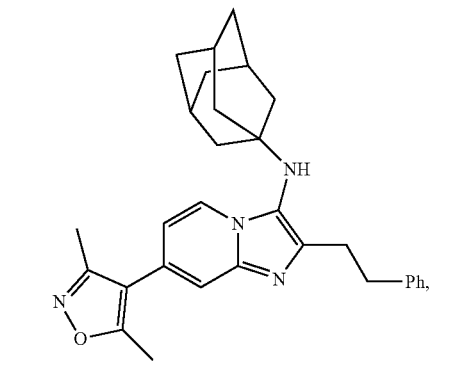

6

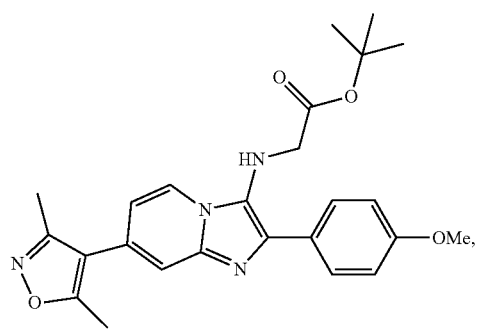
5
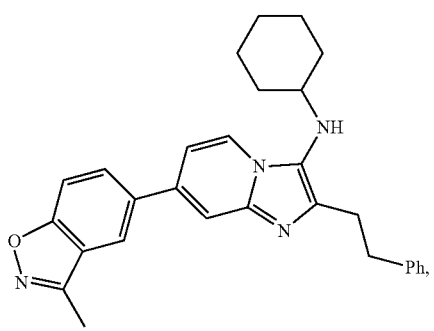
12
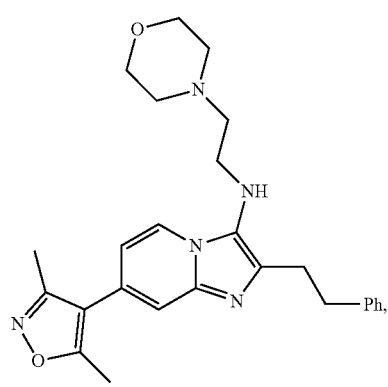
9
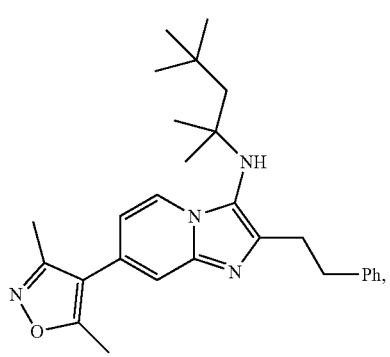
13
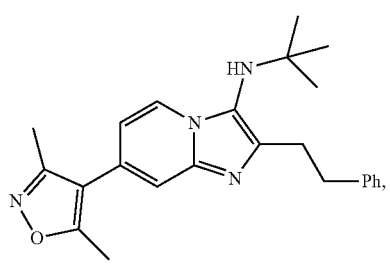
14
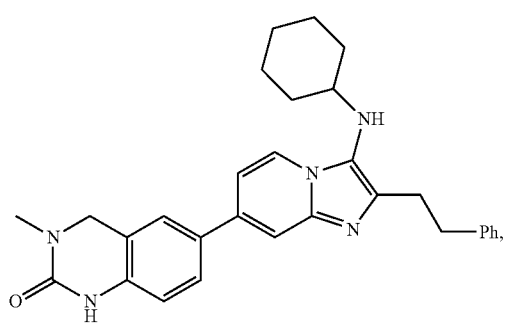
10
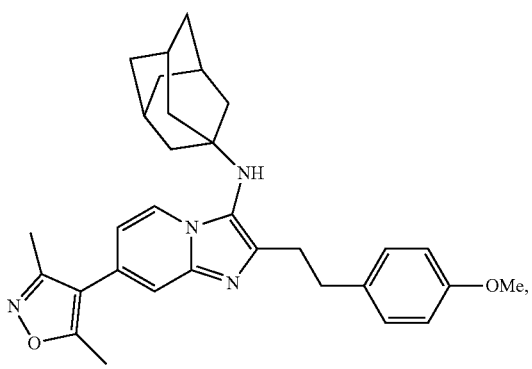
15
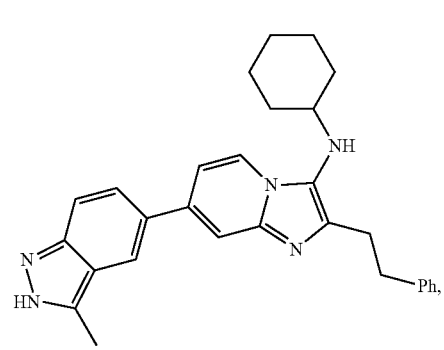
11
16

-continued
17
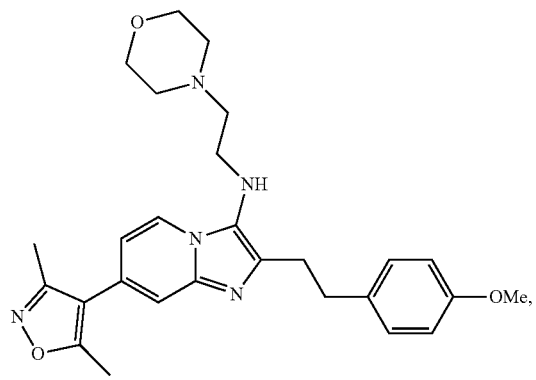
18
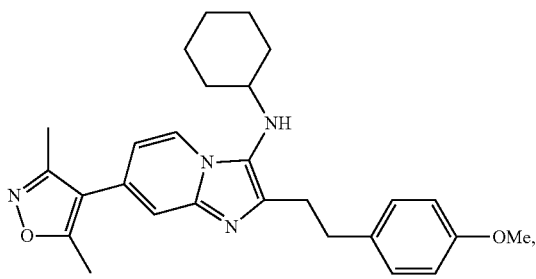
19
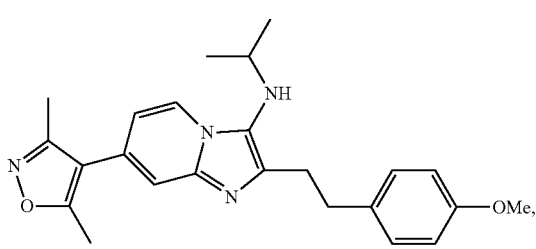
20
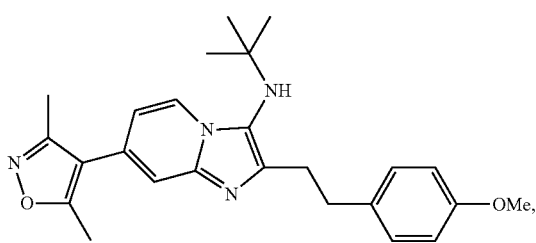
21
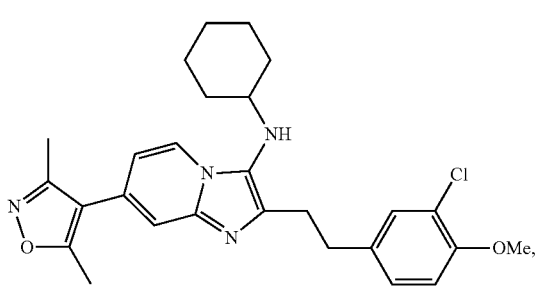
-continued
22
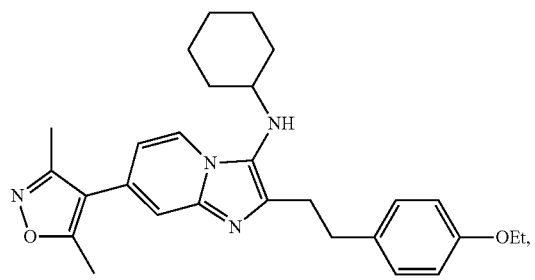
23
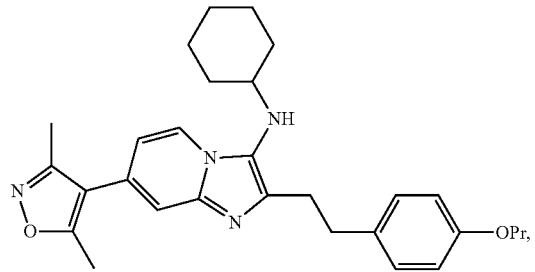
24
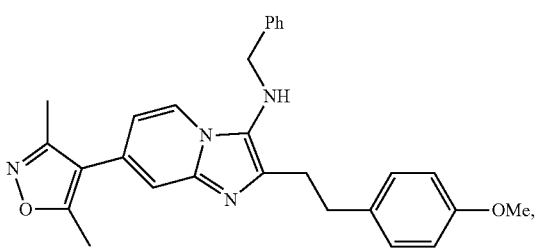
25
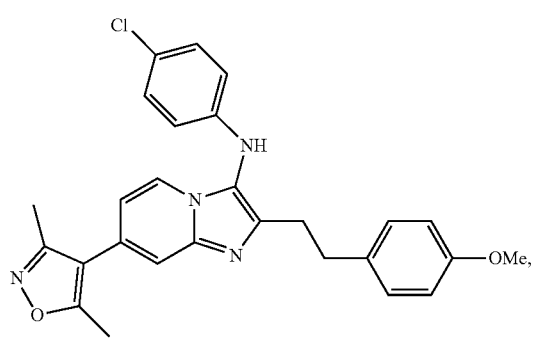

26 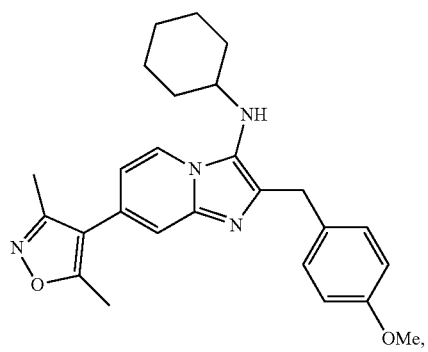
27 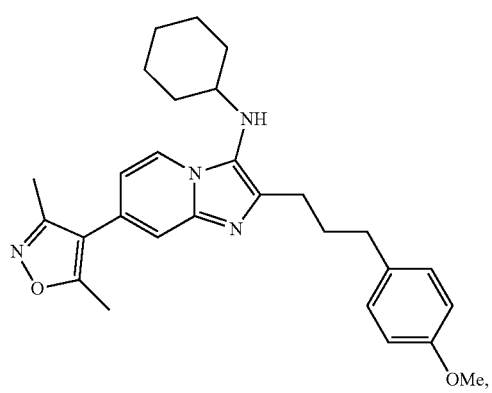
28 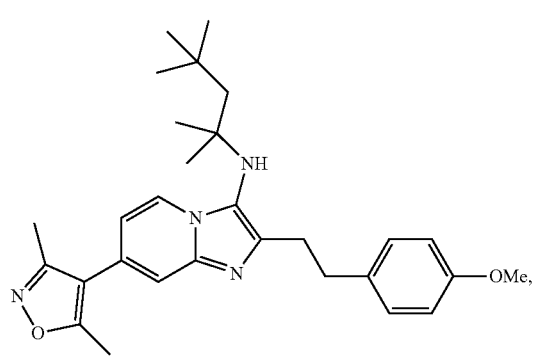
29 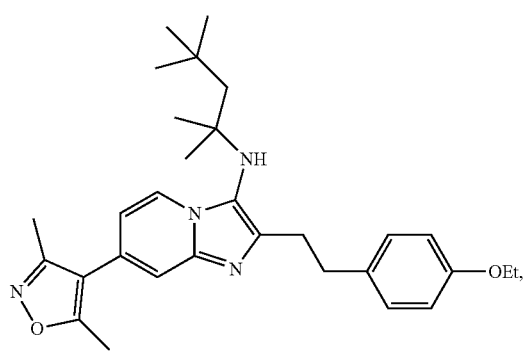
30 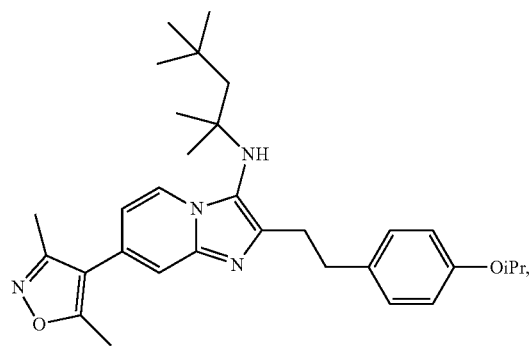
31 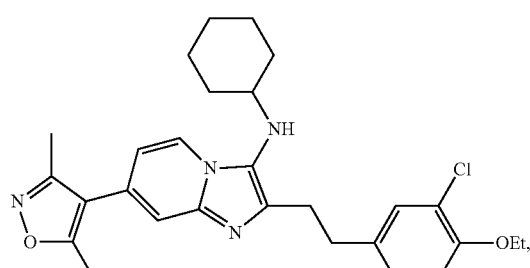
32 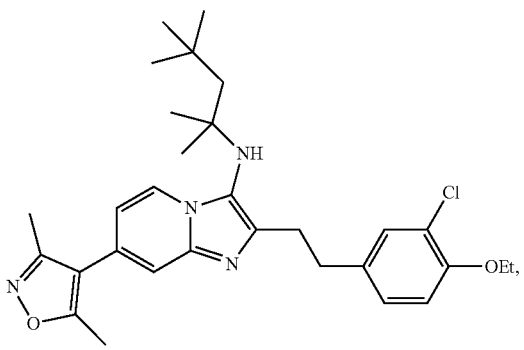
33 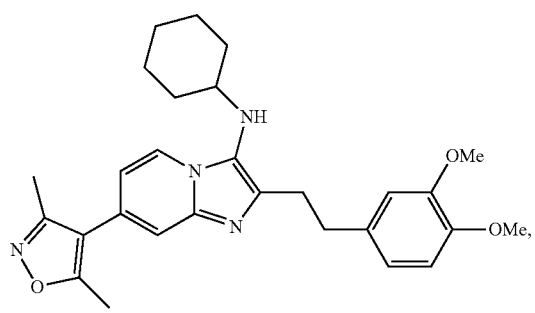

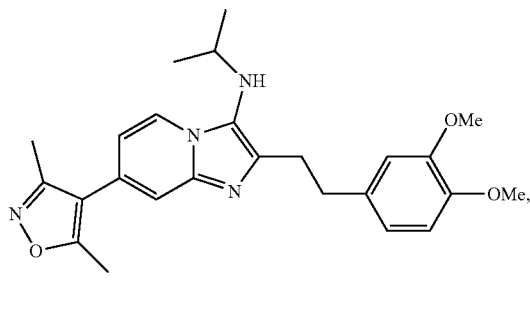

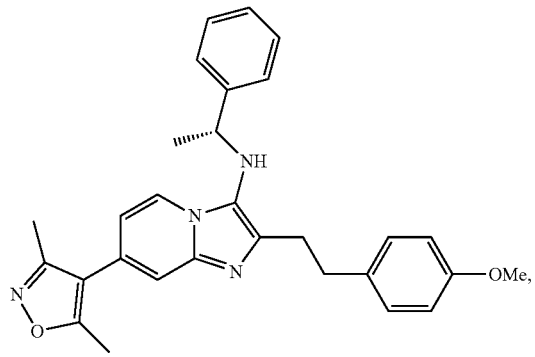

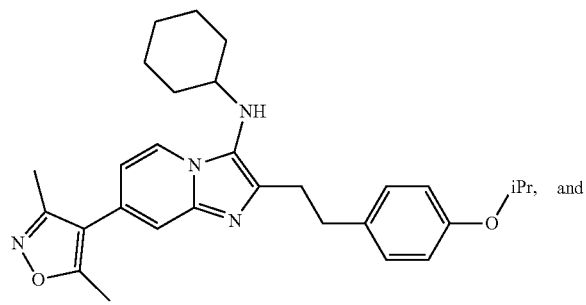

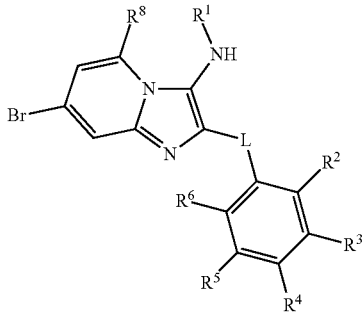

or a pharmaceutically acceptable salt thereof.

23. A pharmaceutical composition comprising a compound of claim 1, or a pharmaceutically acceptable salt thereof, and at least one pharmaceutically acceptable excipient.

24. A method of inhibiting CBP activity, said method comprising contacting a compound of claim 1, or a pharmaceutically acceptable salt thereof with CBP.

25. A process of preparing a compound of Formula I of claim 1, or a pharmaceutically acceptable salt thereof, comprising converting a compound of Formula D:

to afford a compound of Formula I, or a pharmaceutically acceptable salt thereof.

26. The compound of claim 1, wherein n is 1.